US012603165B2

(12) United States Patent
Bernstein et al.

(10) Patent No.: US 12,603,165 B2
(45) Date of Patent: Apr. 14, 2026

(54) PRESCRIPTION DRUG PRICING AND ADJUDICATION SYSTEM

(71) Applicant: Rescription, Inc., Ketchum, ID (US)

(72) Inventors: Gaston Bernstein, Walnut Creek, CA (US); Jeremy Dare, Lake Forest, CA (US); Tyler Monson, Meridian, ID (US); Richard Vaughn, Mandeville, LA (US)

(73) Assignee: Rescription, Inc., Ketchum, ID (US)

( * ) Notice: Subject to any disclaimer, the term of this patent is extended or adjusted under 35 U.S.C. 154(b) by 0 days.

(21) Appl. No.: 18/889,872

(22) Filed: Sep. 19, 2024

(65) Prior Publication Data

US 2025/0014703 A1    Jan. 9, 2025

Related U.S. Application Data

(60) Provisional application No. 63/539,729, filed on Sep. 21, 2023.

(51) Int. Cl.
  *G16H 20/10*    (2018.01)
  *G16H 10/60*    (2018.01)

(52) U.S. Cl.
  CPC ............. *G16H 20/10* (2018.01); *G16H 10/60* (2018.01)

(58) Field of Classification Search
  CPC .............................. G16H 20/10; G16H 10/60
  See application file for complete search history.

(56) References Cited

U.S. PATENT DOCUMENTS

| | | | |
|---|---|---|---|
| 10,720,234 B1 * | 7/2020 | Leonardi | G06Q 30/0207 |
| 11,055,737 B1 * | 7/2021 | Dakic | G16H 50/20 |
| 2002/0087583 A1 * | 7/2002 | Morgan | G06Q 30/06 |
| 2003/0182431 A1 * | 9/2003 | Sturniolo | H04W 76/20 |
| | | | 709/227 |
| 2015/0178807 A1 * | 6/2015 | Tiwari | G06Q 30/0202 |
| | | | 705/26.62 |
| 2015/0242585 A1 * | 8/2015 | Spiegel | G16H 10/60 |
| | | | 705/2 |
| 2021/0065862 A1 * | 3/2021 | Siegel | G16H 20/10 |
| 2021/0174946 A1 * | 6/2021 | Eberting | G06Q 30/0277 |
| 2022/0115105 A1 * | 4/2022 | Nieten | G16H 40/20 |
| 2022/0237677 A1 * | 7/2022 | Ketchel, III | G06Q 50/22 |
| 2022/0261870 A1 * | 8/2022 | Harrell | G16H 40/20 |

* cited by examiner

*Primary Examiner* — Scott C Anderson
(74) *Attorney, Agent, or Firm* — FBT Gibbons LLP

(57) ABSTRACT

Methods and systems are described for adjudicating prescription drug claims and performing price searches and 340b eligibility analyses. An adjudication system can have connections to patients via computing devices or servers, and similar connections to insurers, medical service providers, pharmacies, employers, government information sources, and other service providers. The adjudication system can track prescription and refill information for a patient, notify the patient of better prices at different pharmacies or medical providers, and automatically schedule doctor appointments when refills are needed.

12 Claims, 18 Drawing Sheets

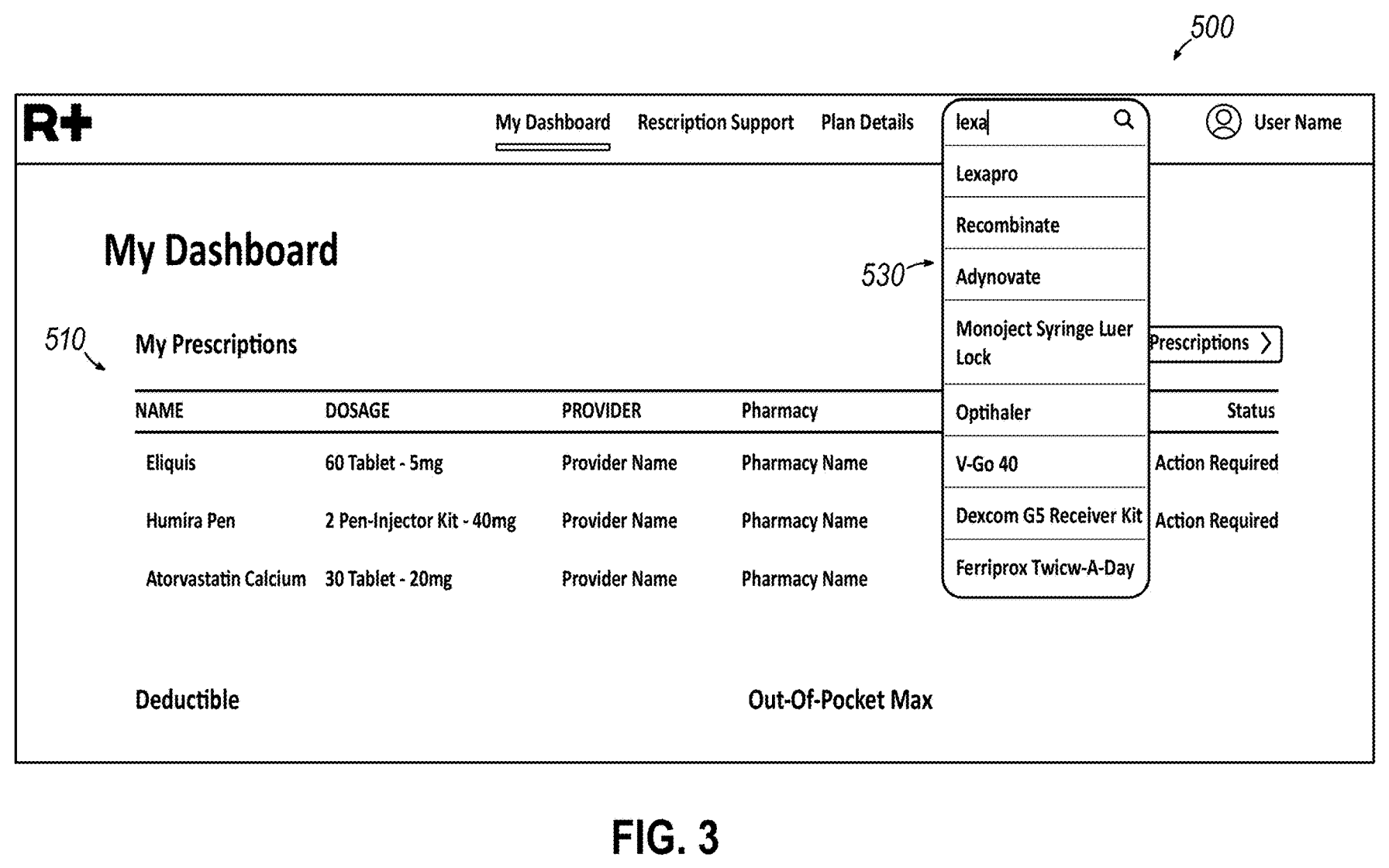

500

◎ User Name

My Dashboard    Rescription Support    Plan Details

My Dashboard

510

My Prescriptions

| NAME | DOSAGE | PROVIDER | Pharmacy | Status |
|------|--------|----------|----------|--------|
| Eliquis | 60 Tablet - 5mg | Provider Name | Pharmacy Name | Action Required |
| Humira Pen | 2 Pen-Injector Kit - 40mg | Provider Name | Pharmacy Name | Action Required |
| Atorvastatin Calcium | 30 Tablet - 20mg | Provider Name | Pharmacy Name | |

| Q | lexa| |
|---|---|
| | Lexapro |
| | Recombinate |
| | Adynovate |
| | Monoject Syringe Luer Lock |
| | Optihaler |
| | V-Go 40 |
| | Dexcom G5 Receiver Kit |
| | Ferriprox Twicw-A-Day |

Prescriptions ⟩

530

Deductible    Out-Of-Pocket Max

FIG. 3

Appointment Availability

| Mon | Tues | Wed | Thurs | Fri | Sat | Sun |
|------|------|------|-------|------|------|-----|
| 9 am | X | 9am | X | X | 9am | X |
| 10 am | 10 am | X | X | X | 10am | X |
| 11 am | 11 am | 11 am | X | 11 am | X | X |
| X | 12 pm | X | 12 pm | 12 pm | X | X |
| 1 pm | 1 pm | X | X | X | X | X |
| X | X | 2 pm | 2 pm | 2 pm | 2 pm | X |

2100

2110

2900

Hidden Layers

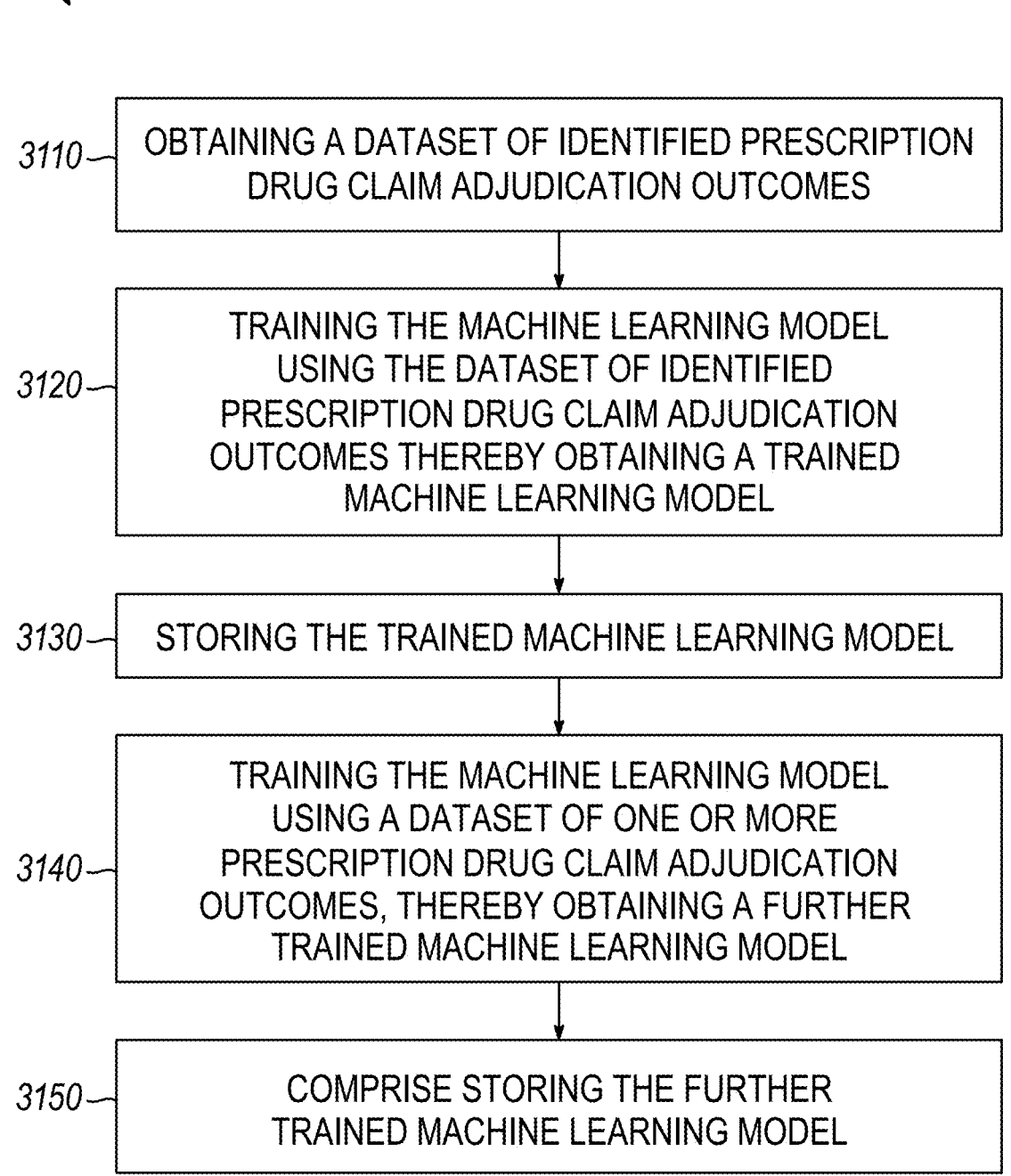

3100

3110 — OBTAINING A DATASET OF IDENTIFIED PRESCRIPTION DRUG CLAIM ADJUDICATION OUTCOMES

3120 — TRAINING THE MACHINE LEARNING MODEL USING THE DATASET OF IDENTIFIED PRESCRIPTION DRUG CLAIM ADJUDICATION OUTCOMES THEREBY OBTAINING A TRAINED MACHINE LEARNING MODEL

3130 — STORING THE TRAINED MACHINE LEARNING MODEL

3140 — TRAINING THE MACHINE LEARNING MODEL USING A DATASET OF ONE OR MORE PRESCRIPTION DRUG CLAIM ADJUDICATION OUTCOMES, THEREBY OBTAINING A FURTHER TRAINED MACHINE LEARNING MODEL

3150 — COMPRISE STORING THE FURTHER TRAINED MACHINE LEARNING MODEL

3310 — INPUTTING ONE OR MORE PRESCRIPTION DRUG CLAIM ADJUDICATION OUTCOMES INTO A TRAINED MODEL, THE MODEL BEING TRAINED USING A FIRST DATASET OF IDENTIFIED PRESCRIPTION DRUG CLAIM ADJUDICATION OUTCOMES

3320 — OBTAINING A SECOND DATASET OF IDENTIFIED PRESCRIPTION DRUG CLAIM ADJUDICATION OUTCOMES IDENTIFIED BY THE TRAINED MODEL.

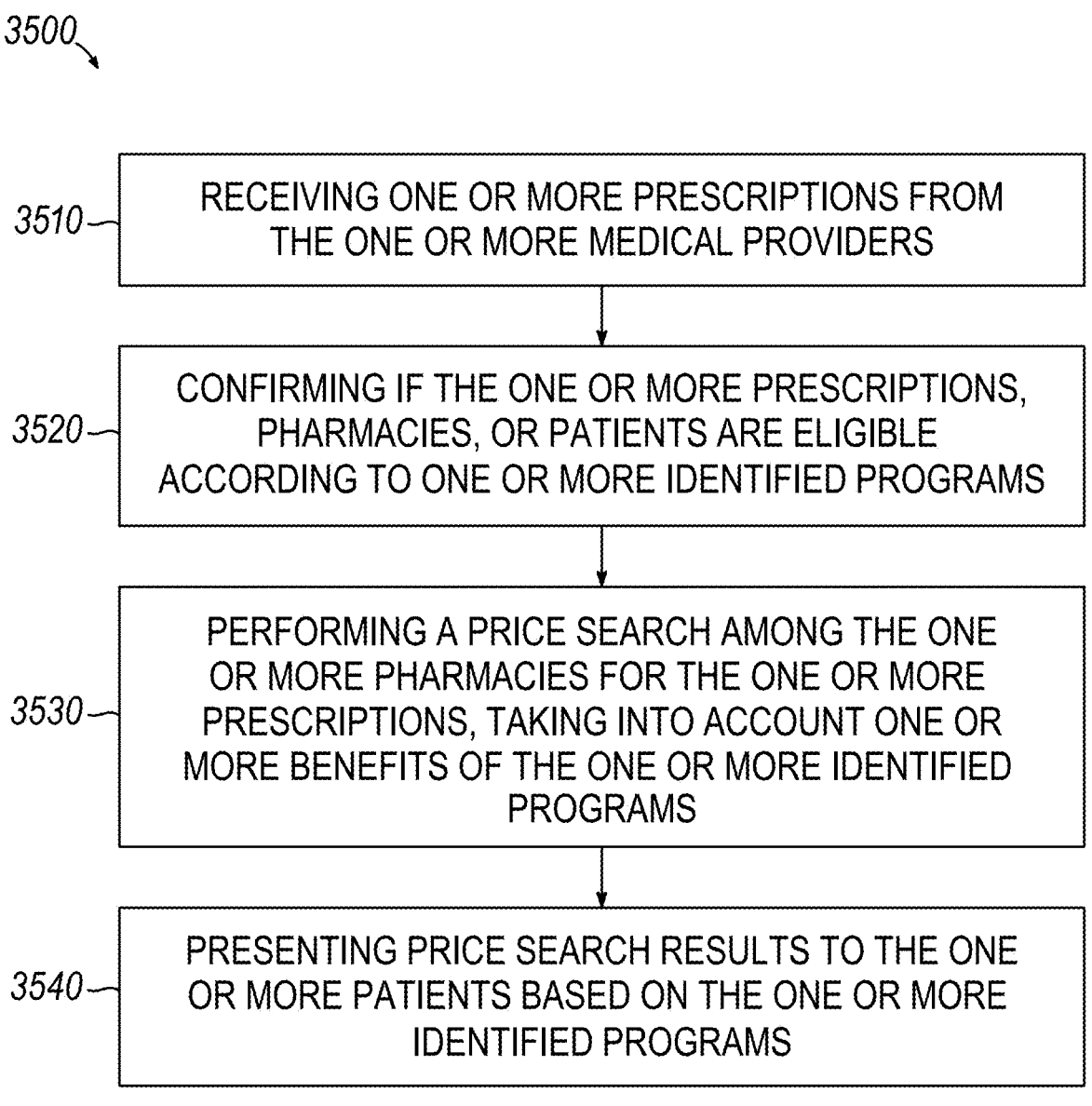

3500

3510 — RECEIVING ONE OR MORE PRESCRIPTIONS FROM THE ONE OR MORE MEDICAL PROVIDERS

3520 — CONFIRMING IF THE ONE OR MORE PRESCRIPTIONS, PHARMACIES, OR PATIENTS ARE ELIGIBLE ACCORDING TO ONE OR MORE IDENTIFIED PROGRAMS

3530 — PERFORMING A PRICE SEARCH AMONG THE ONE OR MORE PHARMACIES FOR THE ONE OR MORE PRESCRIPTIONS, TAKING INTO ACCOUNT ONE OR MORE BENEFITS OF THE ONE OR MORE IDENTIFIED PROGRAMS

3540 — PRESENTING PRICE SEARCH RESULTS TO THE ONE OR MORE PATIENTS BASED ON THE ONE OR MORE IDENTIFIED PROGRAMS

FIG. 18

PRESCRIPTION DRUG PRICING AND ADJUDICATION SYSTEM

CROSS REFERENCE TO RELATED INFORMATION

This application claims the benefit of United States of America priority application No. 63/459,899 filed on Apr. 17, 2023, titled "Prescription Drug Pricing and Adjudication System," and United States of America priority application No. 63/539,729 filed on Sep. 21, 2023, titled "Prescription Drug Pricing and Adjudication System," the contents of which are hereby incorporated herein in its entirety.

TECHNICAL FIELD

The present disclosure generally relates to prescription drug adjudication.

BACKGROUND

It can be difficult for consumers and their employers to locate the best prices for a variety of drugs. This difficulty can especially arise in the case of 340b drugs. The 340b Drug Pricing Program is a federal program requiring drug manufacturers that participate in the Medicaid drug rebate program to provide covered outpatient drugs to enrolled "covered entities" at or below the statutorily defined ceiling price. This requirement is described in Section 340b of the Public Health Service Act and codified at 42 USC § 256b. The 340b Program's purpose is to permit covered entities "to stretch scarce Federal resources as far as possible, reaching more eligible patients and providing more comprehensive services." H.R. Rep. No. 102-384(II), at 12 (1992). To participate in the 340b Program, covered entities must register and be enrolled with the 340b program and comply with all 340b Program requirements administered by HRSA (Health Resources and Services Administration).

SUMMARY

One embodiment under the present disclosure comprises a system for adjudicating prescription drug claims. The system comprises one or more adjudication servers configured to store one or more patient records, the one or more adjudication servers comprising: one or more patient connections configured to communicate with one or more patients; one or more medical provider connections configured to communicate with one or more medical providers; and one or more insurance connections configured to communicate with one or more insurance providers. The adjudication servers can further comprise one or more pharmacy connections configured to communicate with one or more pharmacies; one or more employer connections configured to communicate with one or more employers related to the one or more patients; and one or more government connections configured to communicate with one or more governments. The one or more adjudication servers are configured to: receive one or more prescriptions from the one or more medical providers; confirm if the one or more prescriptions are 340b eligible according to information received from the one or more governments; perform a price search among the one or more pharmacies for the one or more prescriptions; and present price search results to the one or more patients with the one or more patient connections.

Another possible embodiment under the present disclosure comprises a computer implemented method for adjudicating prescription drug claims. The method comprises receiving one or more prescription drug claims for one or more patients; performing preprocessing of the one or more prescription drug claims; saving the one or more prescription drug claims to one or more adjudication servers; and updating preference data related to the one or more prescription drug claims. The method further includes looking up one or more preferred pharmacies related to the one or more patients; looking up one or more pharmacies located near a location associated with the one or more patients or the one or more prescriptions; performing a price search at a preference pharmacy associated with the one or more patients or the one or more prescriptions; sending a test prescription drug claim to each of the one or more preferred pharmacies, the one or more pharmacies, and the preference pharmacy; receiving results for each test prescription drug claim; sorting the results according to price; and saving a lowest price in the results in the one or more prescription drug claims in the one or more adjudication servers.

Another possible embodiment under the present disclosure comprises a system for adjudicating prescription drug claims comprising processing circuitry and a memory. The memory contains instructions executable by the processing circuitry whereby the system is operative to: receive one or more prescriptions from the one or more medical providers; confirm if the one or more prescriptions, pharmacies, or patients are eligible according to one or more identified programs; perform a price search among the one or more pharmacies for the one or more prescriptions, taking into account one or more benefits of the one or more identified programs; and present price search results to the one or more patients with the one or more patient connections.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

For a more complete understanding of the present disclosure, reference is now made to the following descriptions taken in conjunction with the accompanying drawings, in which:

FIG. 3 shows an example embodiment of the user interface of the present disclosure;

FIG. 16 illustrates a flow-chart of a method embodiment under the present disclosure;

FIG. 18 illustrates a flow-chart of a method embodiment under the present disclosure.

DETAILED DESCRIPTION

Figure 1:
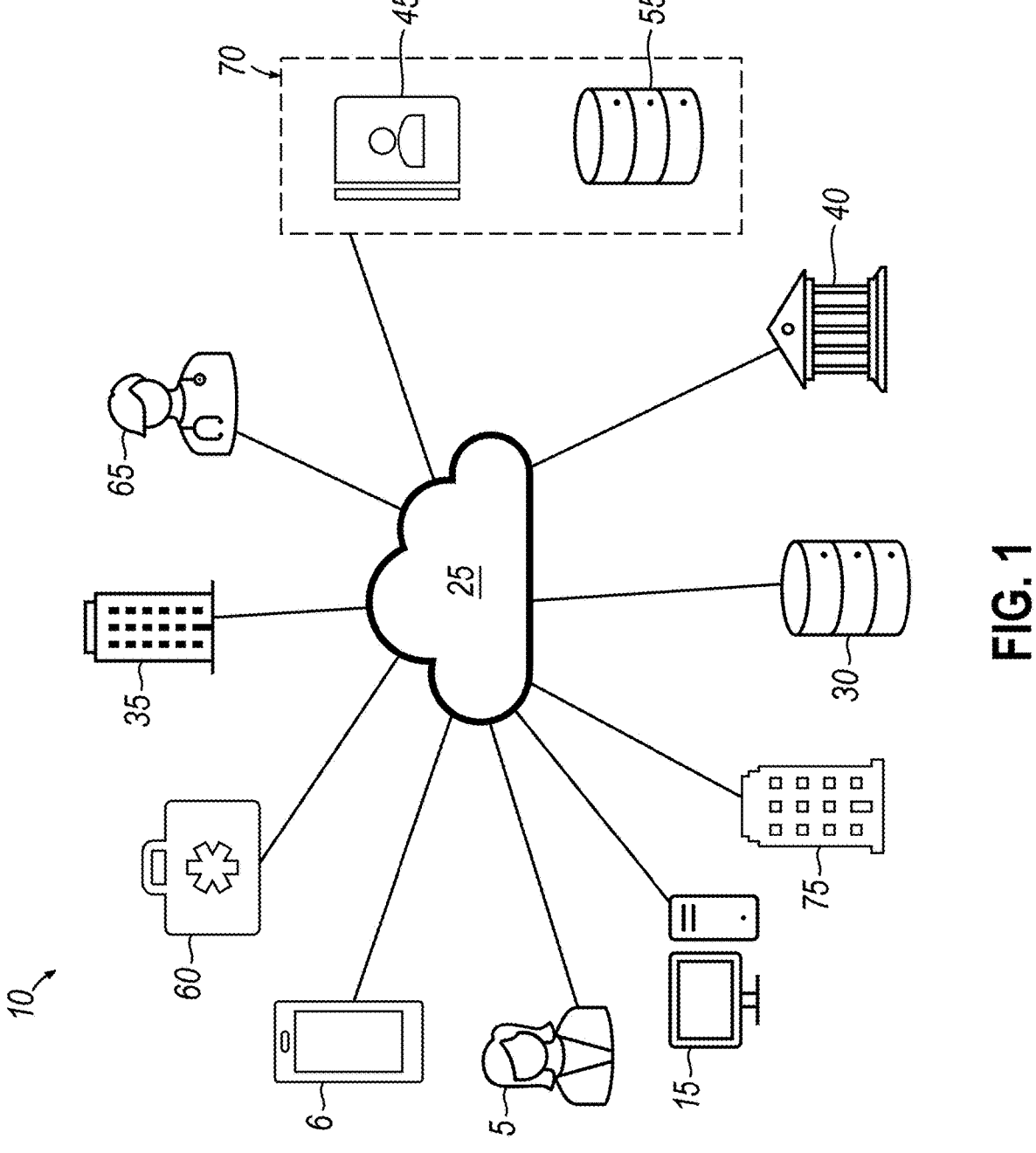
FIG. 1 illustrates one embodiment of a prescription drug price system under the present disclosure.

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed embodiments. In addition, the terminology used herein is for the purpose of describing the embodiments and is not necessarily intended to limit the scope of the claimed embodiments.

There currently exist certain challenges to finding locations, prices, eligibility of 340b drugs, eligibility for other programs, getting prescription refills quickly, scheduling appointments, and payment adjudication for consumers and their employers. For example, getting access to, and finding, 340b covered drugs (or other drug price or payment programs) can be a challenge. But consumers and their employers can save money by determining the location, coverage, and price of 340b drugs. In addition, quick access to drug refills, prescription renewals, and doctors' appointments to obtain refills, can be difficult. However, current pharmacy benefit managers (PBMs) have been unable to provide solutions facilitating the finding and eligibility of 340b drugs while still integrating doctors' appointments and refill capabilities. Only certain locations may comply with, or be eligible for, 340b drugs, for example. Identifying whether consumers are eligible can be difficult as well. To obtain refills, sometimes a consumer has to schedule a doctors' appointment, which can be difficult and time consuming.

Certain aspects of the embodiments disclosed herein provide solutions to these or other challenges. Embodiments include systems and methods for identifying eligible consumers and drugs, finding doctor appointments, requesting refills, as well as identifying specific prices and locations where the drugs are available. This information can help consumers and their employers (who may be at least partially responsible for healthcare costs) to save money.

Certain embodiments may provide one or more of the following technical advantages. Customers and/or their employers and/or their health insurance providers can determine eligibility, price and location of 340b drugs, and/or schedule doctor appointments or request refills, within a single system which can also interface with e.g., pharmacies, PBMs, and/or health insurance companies to determine coverage and perform other adjudication tasks.

In certain embodiments of the present disclosure, a member (e.g., a customer or employer) may search for any drug in a formulary in order to learn more information about it and look up prices at pharmacies for the drug. In order to look up prices, the drug name, form (e.g., tablet, injectable pen, etc.), dosage, days' supply, and quantity (of the form) can be submitted. Drug name, available forms, and available dosages are defined on the formulary, and simple rules allow for the system to know if the maximum supply is 30 or 90 days, but identifying available options for the quantity is much trickier. In order to provide the user guidance for what they can put in for "quantity," the process of the present disclosure analyzes data to return minimum and maximum quantity guidance to the user.

In certain embodiments the present disclosure utilizes a client-specific drug search data hierarchy. The hierarchy structure has been designed to cohesively organize and express drug data from many sources, such as but not limited to drug formulary databases (e.g., CapRx™), client-specific formularies, drug configuration data, drug metadata, and other drug information databases (e.g., Elsevier™), in a single location. A HARD_LIMIT and PER_DAY quantity limit types can be defined, which may distil the quantity limit possibilities from the formulary into those two types. Part of the hierarchy includes a client level. Essentially, because clients are part of the hierarchy, the present disclosure has unlocked large amounts of flexibility in storing drug data such that the data itself could be completely different per client.

The hierarchy enables flexibility and room for evolution at nearly all of its levels. For example, form level of the hierarchy is expandable to contain more information about specific forms. A good example of this is expansion to include data points about quantity limits at the dosage level. The present disclosure can also utilize proprietary or unique representative NDCs (National Drug Code), known as Adjudication Representative NDCs.

The present disclosure can utilize a unique user interface wherein in order to make for a better user search experience, users are not allowed to input invalid quantities. However, this isn't simple web validation. The maximum quantity allowed dynamically changes based on the drug, form, unit of measure, and dosage that are chosen by the user. This feature can be powered by the client-specific drug search data hierarchy. Further, in an effort to help the user better understand the maximum quantity allowed, the present disclosure auto corrects the value entered if they overshot the maximum. Further provided is a dynamic icon popup containing text helping the user better understand the quantity limits for the drug configuration they have chosen. This text is also fueled by data from the Client-Specific Drug Search Data Hierarchy.

FIG. 1 displays one possible embodiment of a prescription drug adjudication, fulfillment and inventory system 10 under the present disclosure. Adjudication system 70 can comprise one or more servers or databases, such as customer account information database 45 (which may store health insurance information, personal information, or other data) and other servers 55 (which may store other information, such as drug information, government regulations or other data, or perform tasks such as adjudication processes, AI/ML models and processes, or other tasks as described herein). Customer 5 may access or receive services from adjudication system 70 via a smart device 6 or other computing device 15 via the internet 25. Internet 25 (or another similarly capable network(s)) can provide communicative coupling between adjudication system 70, customer 5, enterprise 35 (e.g., an employer of customer 5 who provides health insurance), health insurance servers 60 (which may provide access to health insurance coverage/deductible/eligibility/etc. information), medical providers 65 (such as doctor offices, hospitals, etc.), service providers 75 (e.g., CapRx, PBMs, or other medical-related service providers), government servers 40 (or other government databases or resources), and pharmacy servers 30 (which can represent multiple various unrelated pharmacies). Adjudication system 70 may, from time to time, access government servers 40 e.g., for a list of 340b drugs and current prices. Adjudication system 70 may interface with pharmacy servers 30 to e.g., find drug prices and/or to provide coverage information. Adjudication system 70 may interface with medical providers 65 to e.g., provide coverage information or to receive/send drug price or refill information. Adjudication system 70 may interface with service providers 75 to e.g., access or transmit drug or coverage information. Adjudication system 70 may interface with enterprise 35 to e.g., access or provide patient or coverage information related to customer 5. Adjudication system 70 may interface with health insurance servers 60 to e.g., check coverage or deductible information, provide or receive patient drug information, etc. It is to be understood that some service providers or servers illustrated in FIG. 1 may fulfill multiple purposes. For example, some hospitals (medical providers 65) may operate a pharmacy. Such a hospital-based pharmacy may be coupled to adjudication system 70 via pharmacy servers 30 and/or medical providers 65 comprising one or more servers. Each element of FIG. 1 may comprise one or more servers and/or databases for use in communicative coupling with other elements of FIG. 1.

One aspect of certain embodiments comprises providing drug price and searching capability to customer 5 of FIG. 1. FIGS. 2-6 display several possible embodiments of user interfaces provided to a customer by e.g., adjudication system 70 of FIG. 1 to utilized system 10 and access functionality such as: drug price search, 340b eligibility, prescription refilling, pharmacy location and price searching, and more.

Figure 2:
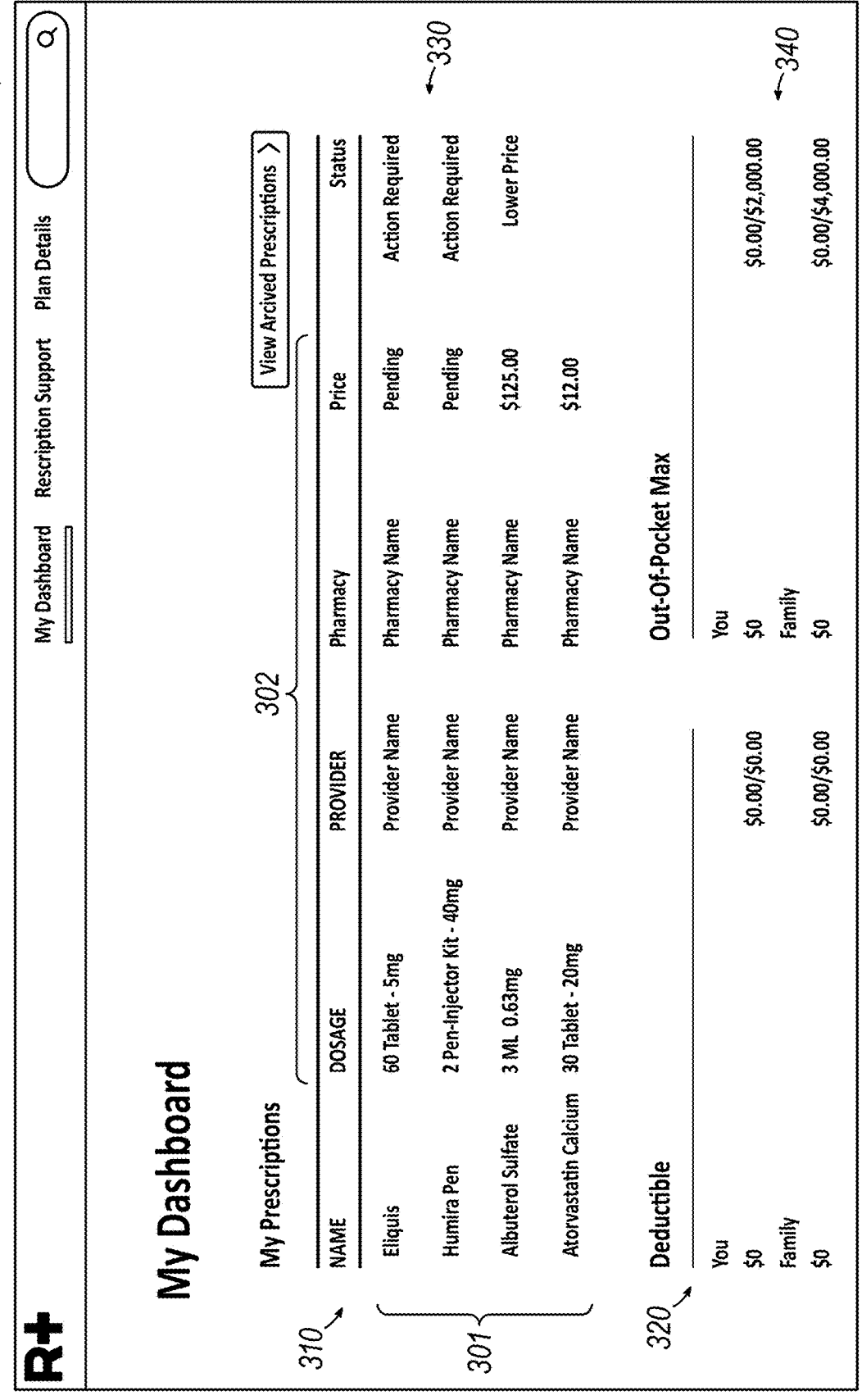
FIG. 2 shows an example embodiment of the user interface of the present disclosure.

FIG. 2 shows an embodiment of a home screen or customer dashboard 300. Prescription list 310 may list various prescriptions 301 that the customer has been prescribed. For each prescription 301 there may be further data 302, such as prescribing doctor, drug amounts, or other information. Prescriptions 301 and/or data 302 may be tracked by adjudication system 70 of FIG. 1, and uploaded or requested from customer 5, medical providers 65, health insurance servers 60, service providers 75, pharmacy servers 30, or from other sources. Deductible information 320 or out-of-pocket cost information 340 may be received or requested from similar sources. Search bar 330 may allow a customer to search for e.g., additional drugs or drug price information.

FIG. 3 illustrates an embodiment of using a search bar 530 to search for additional drugs. User interface 500 also shows a user's prescription list 510. In search bar 530 the user may search for e.g., Lexapro™. As part of the drug price lookup process on the backend, the adjudication system may identify specialty drugs being searched for and inject client-specific preferred provider NPIs (National Provider Identifier) into the price search test claim requests. A user searches for a drug by name in search bar 530 and on the backend (e.g., adjudication system 70 of FIG. 1 interfacing with other providers), using the user context, the adjudication system 70 can identify the user's client code and search for drugs in the OpenSearch instance under the user's client-specific drug search data hierarchy's instance. A list of drug names and drug IDs related to the user's search query can be returned.

Figure 4:
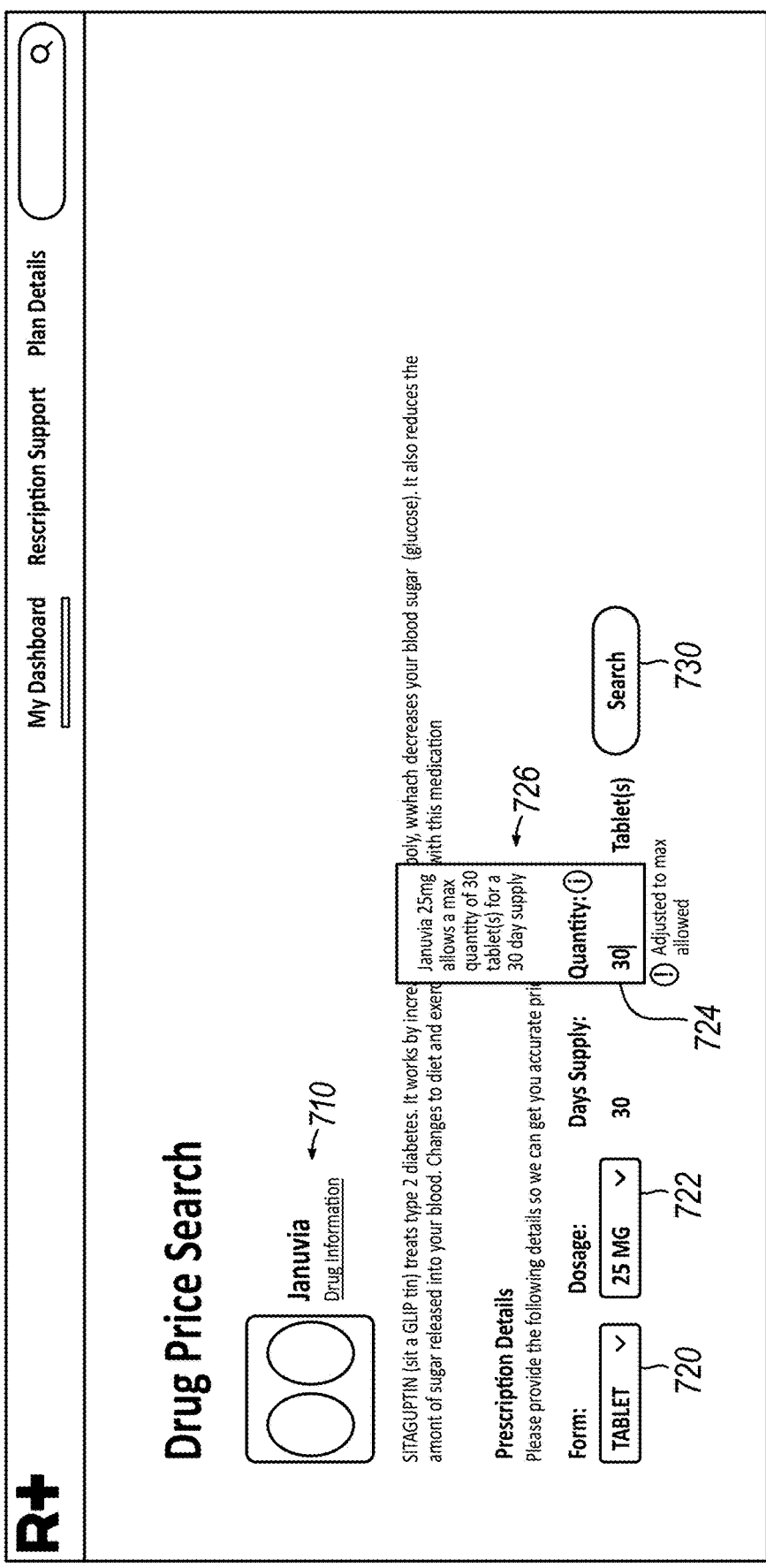
FIG. 4 shows an example embodiment of the user interface of the present disclosure.

The user selects a drug and may be presented with the drug detail page 700 shown in one embodiment in FIG. 4. The drug detail page 700 is loaded and the frontend application/UI may request the drug's data by the drug ID. The backend (e.g., adjudication system 70) returns the drug search hierarchy data matching the drug ID from the client-specific index. The user may configure a drug price search query by selecting further drug data 720 (such as dosage, form, etc.) and selecting search 730. Drug data 720 can take a variety of embodiments, such as form, units of measurement, dosage and more. Drug data 720 can include form, which can be displayed based on the forms contained in the drug search data hierarchy. The user then selects a form and the units of measurement under that form are displayed as options. The user then selects a unit of measurement and the dosages under that unit of measurement are displayed. A dosage is then selected. The custom days' supply field 722 appears and the custom quantity field 724 may be configured based on the data from the dosage selected and the quantity field appears to the user. The field appears with an info icon that shows a popup 726 with dynamic text when the icon is hovered over. The dynamic text of the popup 726 is based on the quantity limit type and quantity limit from the dosage-level data, as well as the days' supply the user entered. The text will vary based on whether the quantity limit type is HARD_LIMIT or PER_DAY. Based on these values, the text can display to the user the maximum limit that can be entered in the quantity field. If the value entered by the user is under the minimum quantity or over maximum quantity (maximum quantity depends on the dosage chosen) allowed, the field will be autocorrected for the user (either to the minimum or the max depending on which was breached). A message can appear to let the user know their value was adjusted.

Figure 5:
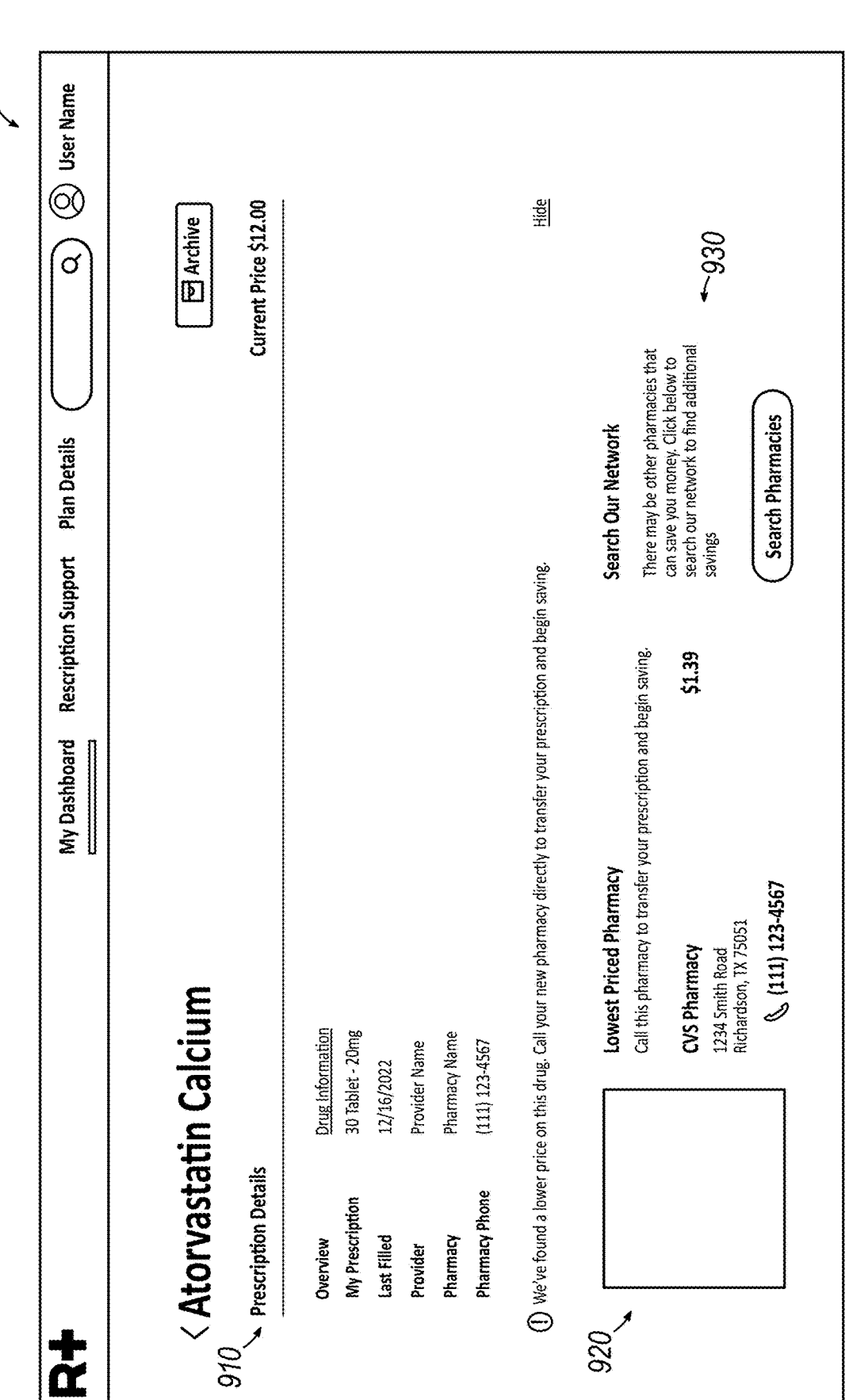
FIG. 5 shows an example embodiment of the user interface of the present disclosure.

Instead of searching for a new drug from search 330 of FIG. 2, a user may click on one of their existing prescriptions 301 to access a prescription information page. An embodiment of a prescription information page 900 is shown in FIG. 5. Prescription details 910 can be shown with filing dates, pharmacy information, and other data. In one or more embodiments of the present disclosure, when a pharmacy submits a claim and it is adjudicated as paid (e.g., the claim is successful and the patient is able to get their drug), after this process is completed the adjudication system 70 of FIG. 1 can run a "market check" for the patient. Certain embodiments of the present disclosure can e.g., search all other pharmacies that the patient could have "reasonably" chosen to get this drug at (e.g., this could be defined as pharmacies within 10 miles of the retail pharmacy where they picked it up and any available mail order option) and run test claims for that drug at each of these pharmacies to see what the price would have been if the patient had gone there instead. If any of these checks result in a lower price, the present disclosure can notify the patient through a push notification and screens in the application to let them know that next time they could save money on that drug by using the other pharmacy. One embodiment of notification 920 is shown below prescription details 910. The present disclosure can also comprise a configurable setting that allows for a minimum savings threshold to be set under which the system would not notify the patient of any potential savings. The user can select the search button 930 to find additional pharmacies that may provide savings.

Figure 6:
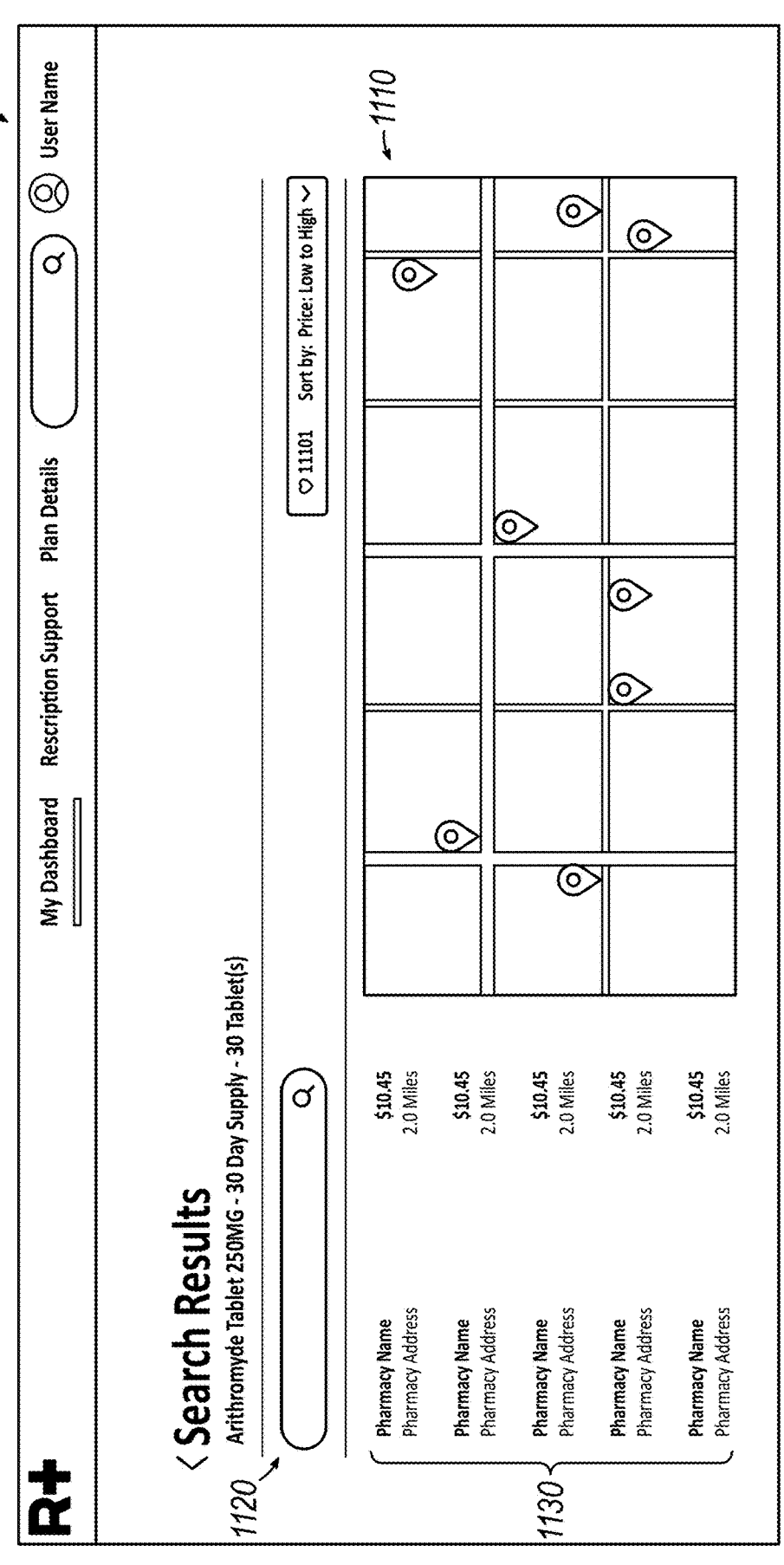
FIG. 6 represents an example screen shot of the user interface after the local price search has been completed.

Selecting search 930 of FIG. 5 or search 730 of FIG. 4 may lead to a search screen 1100, one embodiment of which is seen in FIG. 6. Search screen 1100 can comprise a map 1110, settings bar 1120, and search results 1130. Map 1110 may show various pharmacy locations in e.g., a selected radius or zip code. Settings bar 1120 may allow the user to e.g., adjust a radius, adjust a zip code, search for specific pharmacies, or adjust other settings. Search results 1130 may display e.g., pharmacy names, locations, and prices. Adjudication system 70 of FIG. 1, for example, may store map and location data of various pharmacies, or may in real-time or from time to time access such information from pharmacy servers 30 or other information sources in FIG. 1. Drug price information similarly may be retrieved or stored by adjudication system 70 from pharmacy servers 30 or other information sources and then be presented to the user such as through e.g., search screen 1100. The price checking process of the present disclosure can check prescription prices at multiple pharmacies (including plan preferred pharmacies), using live member plan data to determine the actual member cost, immediately after a claim has been adjudicated. This process uses pharmacies near the original pharmacy, plan preferred pharmacies, adjudicated test claims, preferred providers, or other pharmacies into the price search to unlock specialty drug preferred prices. This allows for accurate pricing based on the plan member the test claim is made for and is crucial in determining whether the member can get preferred pricing for specialty drugs. In one or more embodiments, a lowest price tie breaking sorting/method is used to break ties between pharmacies that have the same price for the drug being searched.

A user of search screen 1100 can select a pharmacy with the lowest cost, or select a pharmacy based on other variables, and adjudication system 70 can transfer or submit the selected prescription to the desired pharmacy and complete the adjudication process, asking the pharmacy to fill the prescription and interface with e.g., insurance provider 60 and pharmacy servers 30 to update refill information, deductible information or other data. In certain embodiments, the live feed of claims into the system of the present disclosure allows for the sending of notifications (e.g., email, text, push, or other notifications) for prescription holds. Additionally, a ticket creation (e.g., via Zendesk™) can be utilized for prescription holds and specialty drug refills needed. Embodiments of the present disclosure can also utilize preferred discrepancy detection.

FIGS. 1 to 6 have provided an overview of adjudication system 70 and the operations of the overall prescription drug system 10, and a user interface for a user. Further detail is given below on e.g., the internal operations of e.g., prescription drug adjudication, fulfillment and inventory system 10 and/or adjudication system 70 and how several functionalities described above can be implemented. Reference is made in the description to different cloud environments (e.g., certain AWS™ (Amazon Web Services)) or other third-party tools, functionality, and data types. These are just for illustrative purposes and the present disclosure can be implemented in a variety of environments.

Figure 7:
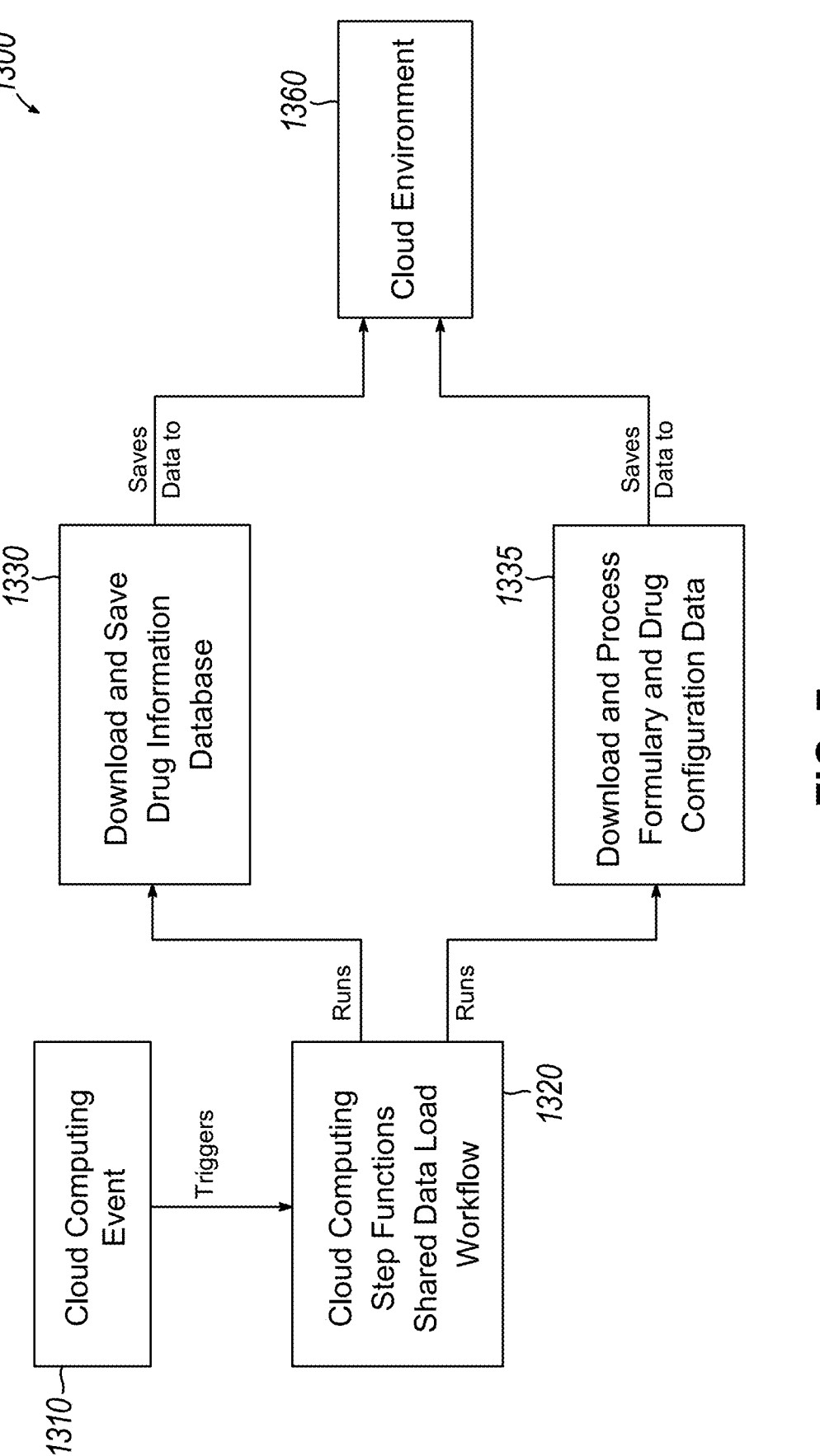
FIG. 7 shows how Shared Drug Data is loaded within the system of the present disclosure.

FIG. 7 illustrates one possible embodiment of a process flow 1300 for how shared drug data is loaded. In certain embodiments, once a month, a cloud computing event (e.g., AWS EventBridge) event 1310 triggers a cloud computing shared data load workflow (e.g., AWS Step Functions) 1320 that downloads drug metadata, images, and patient education information from a drug information database (e.g., Elsevier) at 1330 and stores it all in cloud environment 1360 (e.g., an AWS S3 bucket) in a Client-Specific Drug Search Data Hierarchy. Next, formulary and drug data (e.g., CapRx) 1335 is fetched and combined at 1335 and saved in cloud environment 1360. The full formulary is pulled from cloud storage; then a set of unique NDCs is generated using the NDCs from the formulary file. Next, the list of unique NDCs can be used to fetch drug configuration (drug configuration consists of drug name, form, unit of measure, dosage, package quantity, etc.) information from the formulary API (e.g., CapRx API). After fetching the data, there may be one data object (e.g., JSON (Javascript Object Notation)) for every NDC from the unique list of NDCs. Related days' supply/quantity limit data from the formulary can be injected into each of the drug configuration data objects using the drug configuration NDC. The drug configuration can be matched to the most recent formulary entry for that drug configuration. If the most recent formulary entry does not have quantity limit data, the drug configuration can be injected with undefined quantity limit type and quantity limit values. These values can be set during the Client Drug Data Load process.

If the most recent formulary entry does have quantity limit data, the adjudication system can analyze the data to determine if the quantity limit type should be set to a HARD_LIMIT or a PER_DAY value. HARD_LIMIT and PER_DAY are quantity limit designations unique to the present disclosure. If HARD_LIMIT is chosen, the quantity limit of the drug configuration is set to the quantity limit extracted from the formulary entry. Some quantity limits in the CapRx formulary are designated as per prescription (ex: 100/rx). The adjudication system can identify and label these with the HARD_LIMIT quantity limit type. IF PER_DAY is chosen, the quantity limit of the drug configuration is set to the extracted quantity limit divided by the quantity limit days (e.g., per day quantity limit=formulary quantity limit/ formulary quantity limit days). Drug configuration data with its injected days' supply/quantity limit data is saved as a single e.g., JSON file to an cloud environment bucket to be used with each Client Drug Data Load.

Figure 8:
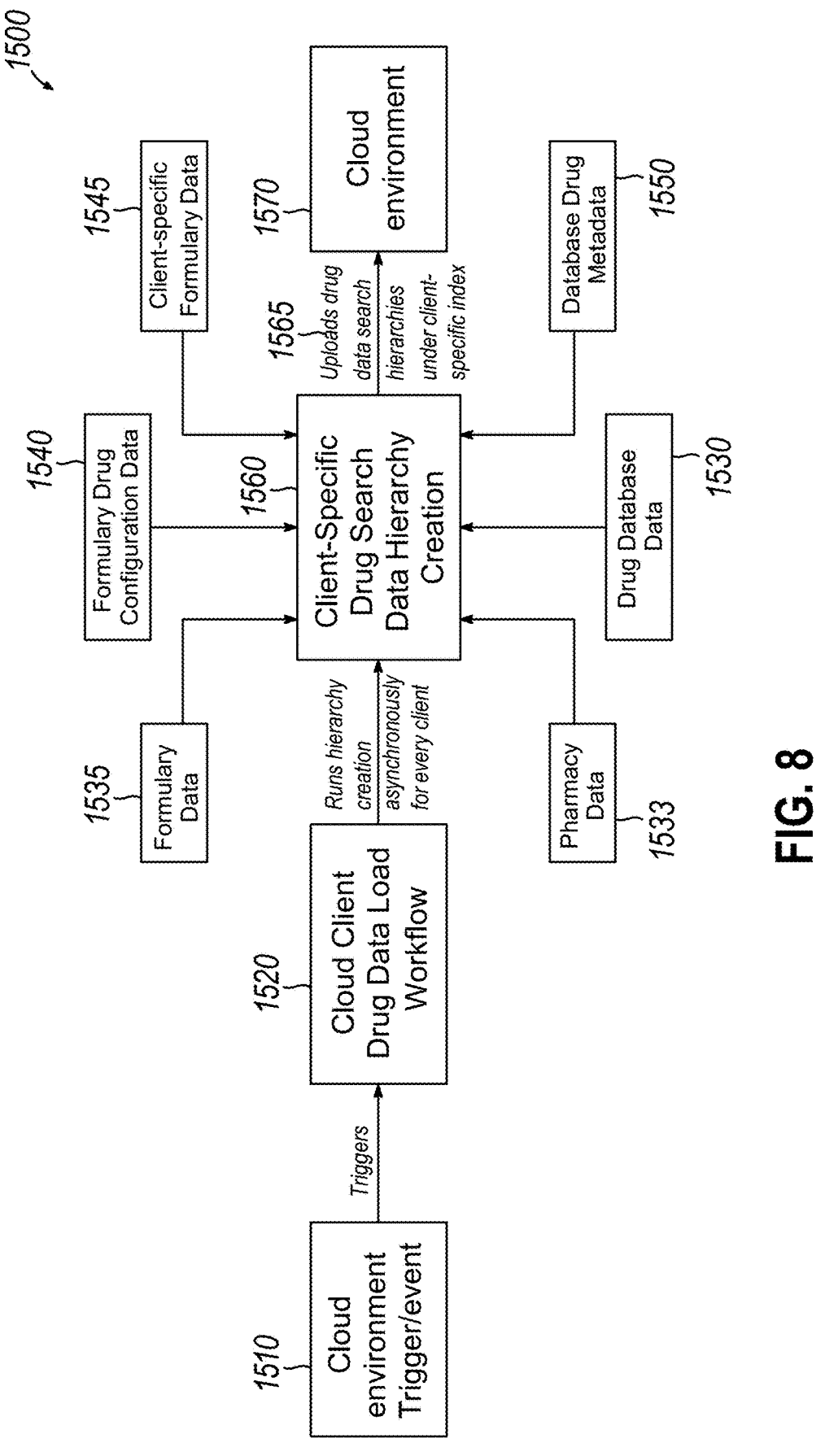
FIG. 8 shows how the Client Drug Data is loaded within the system of the present disclosure.

FIG. 8 illustrates one method embodiment 1500 of how the client drug data is loaded. Once a month (e.g., minutes after the Shared Drug Data Load completes, and other delays or time periods/periodicity are possible), an cloud event 1510 triggers a cloud client drug data load workflow (e.g., AWS Step Functions workflow) 1520 that gathers the full list of clients utilizing the system and asynchronously runs each of them through the following drug search data hierarchy construction/transformation. First, the drug configuration 1535, 1540 and drug database (e.g., Elsevier) package data 1530 is pulled from the cloud buckets they were saved to during the Shared Drug Data Load shown in FIG. 7. A client-specific formulary file 1545 (each client has their own unique file) is then downloaded from a cloud storage bucket (e.g., AWS S3). Drug configurations are filtered out based on the client-specific formulary file and only drug configurations that can be matched to an NDC on the client-specific formulary file are referenced in the rest of this data transformation. Pharmacy data can be uploaded as well at 1533. Pharmacy data can pulled from a pharmacy database or other resource (e.g., CapRx).

Drug configurations are matched to drug database data points by NDC. When an drug database data match is found, the present disclosure injects the drug configuration with drug image, package, and patient education data at 1550. Drug configurations themselves are combined into a custom-designed drug data hierarchy foxued on naturally supporting the User Interface drug search workflow. All drug configurations with the same drug name combine into a single drug search hierarchy. Each drug search hierarchy is assigned a unique ID, which is computed by taking a SHA-2 (Secure Hash Algorithm 2, e.g., SHA256) hash of the drug name. The hierarchy can then be organized as, e.g., Simplified hierarchy: Drug name→1 or more drug forms→1 or more drug units of measurement→1 or more dosages→dosage level drug metadata. The top (Drug name), forms, and dosages levels of the hierarchy can hold any number metadata points to enrich that level of the hierarchy. With such a structure the present disclosure is able to store complex expressions of drug configurations in one data object. Further, the complex expressions of drug configurations flow naturally with the workflow of the user interface (user picks drug by name, selects form, selects unit of measurement, selects dosage, etc.).

While combining drug configurations into these drug search data hierarchies, the present disclosure chooses the appropriate quantity limit type and quantity limit values at the dosage level for each dosage in each hierarchy. If the drug configuration being merged into the drug search hierarchy does not have quantity limit values, it is assigned a quantity limit type of HARD_LIMIT and it is assigned a quantity limit equal to its package size for the data merge process. If the drug configuration being merged into the drug search hierarchy does have quantity limit values, those values are used in the data merge process. This essentially becomes a set of default values. Formulary quantity limit values take precedence over default values.

In general, if default values are being merged against default values or formulary values are being merged against, the larger quantity limit value will win and be attached to the drug data search hierarchy. Specialty drugs quantity limit values trump standard default or non-specialty formulary values. Using a custom defined mapping of drug forms to quantity qualifiers, quantity qualifiers are also set at the dosage level. NDC is also set at the dosage level. NDCs are chosen using the same rules used for determining quantity limits, e.g., the NDC with the highest quantity limit is always chosen, of course, always still giving precedence to specialty drugs.

As a final step in the process of constructing drug data hierarchies, the present disclosure marks drug search hierarchies as specialty drugs at the dosage level using specialty drug metadata defined in the database discussed above to identify the points that should be marked as specialty. Drug search data hierarchies are sorted at the form, unit of measurement, and dosage levels. Drug search data hierarchies are then loaded into a client-specific index at 1565 in cloud environment 1570 (e.g., an AWS OpenSearch instance). With each client drug search data hierarchy set being saved under a unique client index in the cloud environment 1570, the present disclosure is able to have drastically different drug search data sets per client. This allows the present disclosure to provide unique sets of searchable drugs per client. Further, it allows the present disclosure to vary drug metadata per client at every level of the hierarchy.

Figure 9:
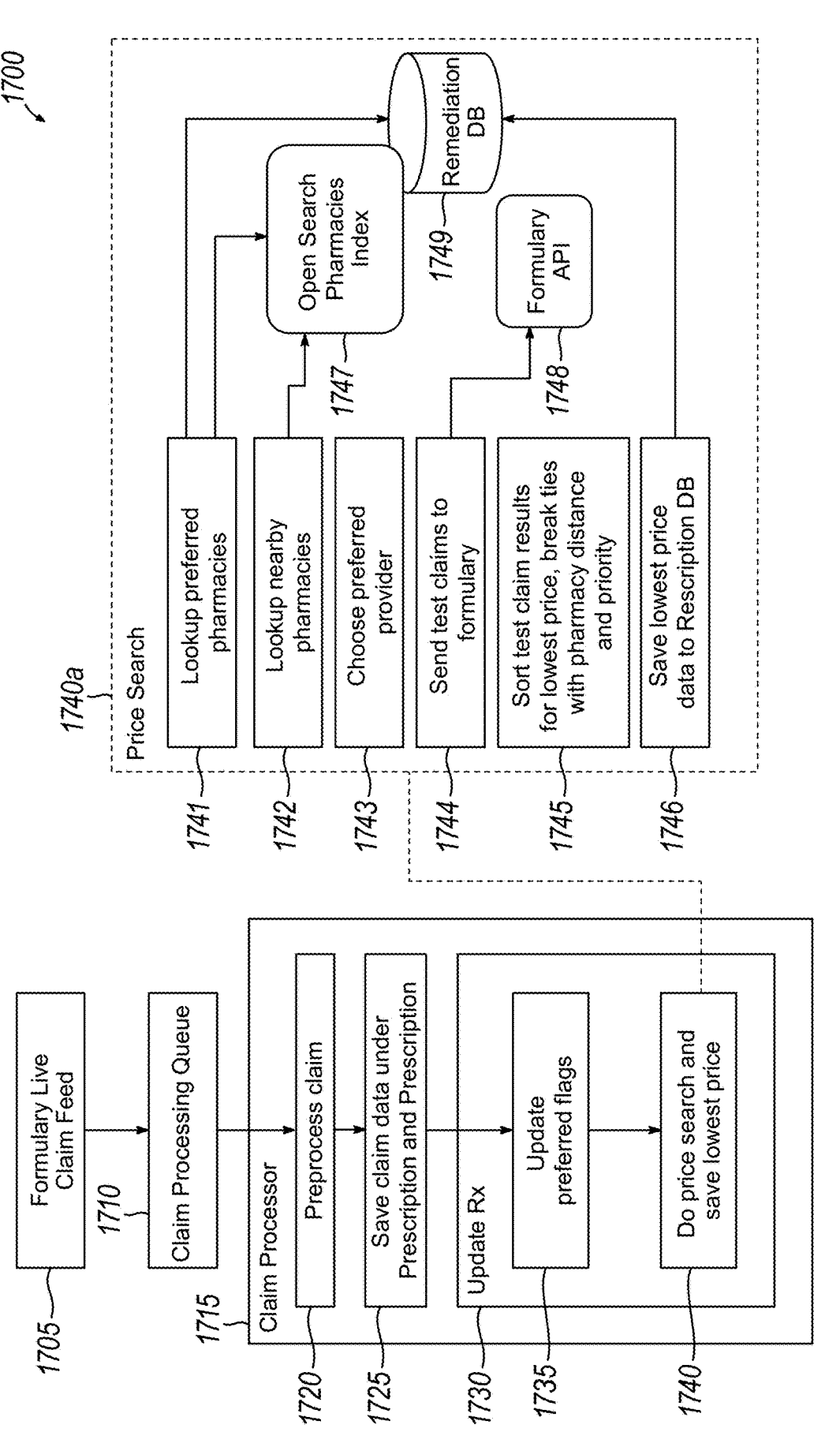
FIG. 9 shows an example embodiment of the post-adjudication price check of the present disclosure.

FIG. 9 shows an example embodiment of the post-adjudication price check process 1700 of the present disclosure. First, at 1705, drug formulary (e.g., CapRx) provides a live feed of all prescription claims related to client accounts. Claims from the formulary arrive on a secure queue (e.g., AWS SQS FIFO (first in first out)) at 1710. All received claims trigger claim processing logic (powered by e.g., AWS Lambda) at 1715. Each claim can initiate its own claim processing logic. The claim processing logic parses and extracts the claim payload from the SQS message and then runs preprocessing tasks against the claim at 1720. The preprocessing 1720 can include, e.g.: logging that the claim was received in the database; creating a Prescription On Hold ZenDesk ticket if necessary; creating a Prescription Needs Refill Zendesk ticket if necessary; updating a 340b flag on the claim in the CapRx system if necessary; removing a 340b flag on the claim in the CapRx system if necessary; and detecting preferred discrepancies using a preferred drug, pharmacy, and provider database data as the source of truth and notifying relevant individuals if a discrepancy is found. For example, if the claim should have been preferred rejected by the drug formulary or if it should NOT have been rejected by the drug formulary, an email can be sent to an arbitrary group of people with details about the discrepancy.

Next, the system links the claim to a user, if no user is found, the processing ends. If a user is found, a data object is created in the database if the user has never had a drug with this name before. The claim data can be saved at 1725 as a data object in the database under the data object. The claim data is then updated (update process 1730) with preferred flags 1735 and price check data 1740. Updating the price can comprise e.g., a method 1740a for checking price data. This price check data is used to mark whether the claim data has a preferred provider. It also uses data from the database to mark whether the claim data has a preferred pharmacy. Data from the formulary API is additionally used to add provider details (name and phone number) to the claim data. Finally, a local price search for the drug is undertaken. The local price search uses data from a remediation database 1749 (which may comprise e.g., adjudication system 70 of FIG. 1) and pharmacies OpenSearch data 1747 to find all preferred pharmacies (and e.g., location information) for the user and claim combination at step 1741. The local price search then uses the pharmacy OpenSearch data to find a desired number (e.g., 5 or 10) non-preferred pharmacies near the claim's original pharmacy at step 1742. The local price search then chooses a preferred provider to do a price search at step 1743. If the claim had a preferred provider on it as the prescriber, that provider is used. A preferred provider can also be chosen based on the user and the drug the claim represents. A test claim is then sent to the formulary at 1744 for every pharmacy (injecting the preferred provider into the test claim) for the drug the claim represents. This can be done via e.g., a CapRx API 1748.

The local price search then finds the lowest price from the test claim results at 1745, choosing the best price based on some desired or preset priority, e.g.: Price; Distance from the original pharmacy; and Pharmacy priority (a value designated to preferred pharmacies). The local price search then saves, at 1746, the lowest price data to the claim data in the remediation database 1749 so it can later be displayed to the user. In certain embodiments, if the claim represents a 340b drug, then the user is marked as a 340b patient in the remediation database 1749. Finally, the local price search sends on hold notifications and updates. In certain embodiments, this is done using AWS SNS (Simple Notification Service) to send "On Hold" prescription push notifications and/or an email if the claim being processed represents a new claim that has been put on hold for preferred reasons. In certain embodiments, the local price search can use an AWS SNS background push notification to update the number of on hold prescriptions displayed to the user on their mobile app. FIG. 6, discussed above, represents an example embodiment of the user interface of search screen 1100 after the local price search has been completed.

In one or more embodiments, the pharmacy search data load at step 1742 utilizes an AWS EventBridge event to start the data load by launching a pharmacies import Step Functions workflow. The workflow includes pulling all pharmacies from the pharmacy database API (e.g., CapRx); transforming their data format; and putting location latitude and longitude under the location property. Additionally, the workflow defaults the pharmacies preferred property to "N" (NONE) and the pharmacy type to "R" (RETAIL). Finally, uploading of all of the pharmacies under a pharmacies index can occur in a cloud environment (e.g., anAWS OpenSearch instance).

The methods and functionalities described in FIGS. 7-9, or in other embodiments described below, can be performed entirely, or in part, by prescription drug adjudication, fulfillment and inventory system 10 and/or adjudication system 70.

In certain embodiments of the present disclosure, when a prescription claim is submitted by a pharmacy (e.g., pharmacy servers 35 in FIG. 1) into a claim adjudication system (e.g., 70 of FIG. 1) of the present disclosure, the initial step is to run a check to see if the claim is "340b compliant" (or check if the drug/claim is listed on a preferred list of an employer, or is otherwise identified by an employer or the system for special treatment). The first step of this process can be to determine if the drug is on the list of 340b-qualifying drugs received or pulled from e.g., government servers 40 of FIG. 1 (or to determine if the drug is on e.g., a client-specific list). If yes, then the adjudication system 70 can check the doctor unique ID number and pharmacy unique ID number against a predefined list of approved doctors and pharmacies. If both the doctor and pharmacy are on the list(s), then the adjudication system 70 can apply special 340b adjudication rules. If one or the other isn't on the list, then the prescription is put into an "on hold" state which triggers notifications for the required actions.

In certain embodiments, adjudication system 70 can perform, or use a service provider 75 (e.g., a PBM) a tag/override system to do these checks. The check is preferably client specific, so the lists of specialty drugs, preferred pharmacies, and preferred providers can be different per e.g., pharmacy benefit manager client/plan. Given this, the preferred pre adjudication checks process is handled by the adjudication system 70 managing its own tag/override system.

In certain embodiments, a tag/override system (operated in adjudication system 70 or service provider 75) may receive a prescription claim from pharmacy servers 35. If the claim can be linked to a known plan/client that is known as 340b compliant or eligible, e.g., stored by servers 55 of adjudication system 70, and if the drug that claim represents is on the list of 340b eligible program drugs for that client, then the claim's prescriber is checked against the client's list of preferred providers. Next, the claim's pharmacy is checked against the client's list of preferred pharmacies. If the claim's prescriber or pharmacy (or both) are not on the preferred lists, the claim can be rejected, e.g., with an 828 reject code. Finally, if the claim's prescriber and pharmacy are both on the preferred lists, the claim proceeds through as normal into other claim processing/checks.

Figure 10:
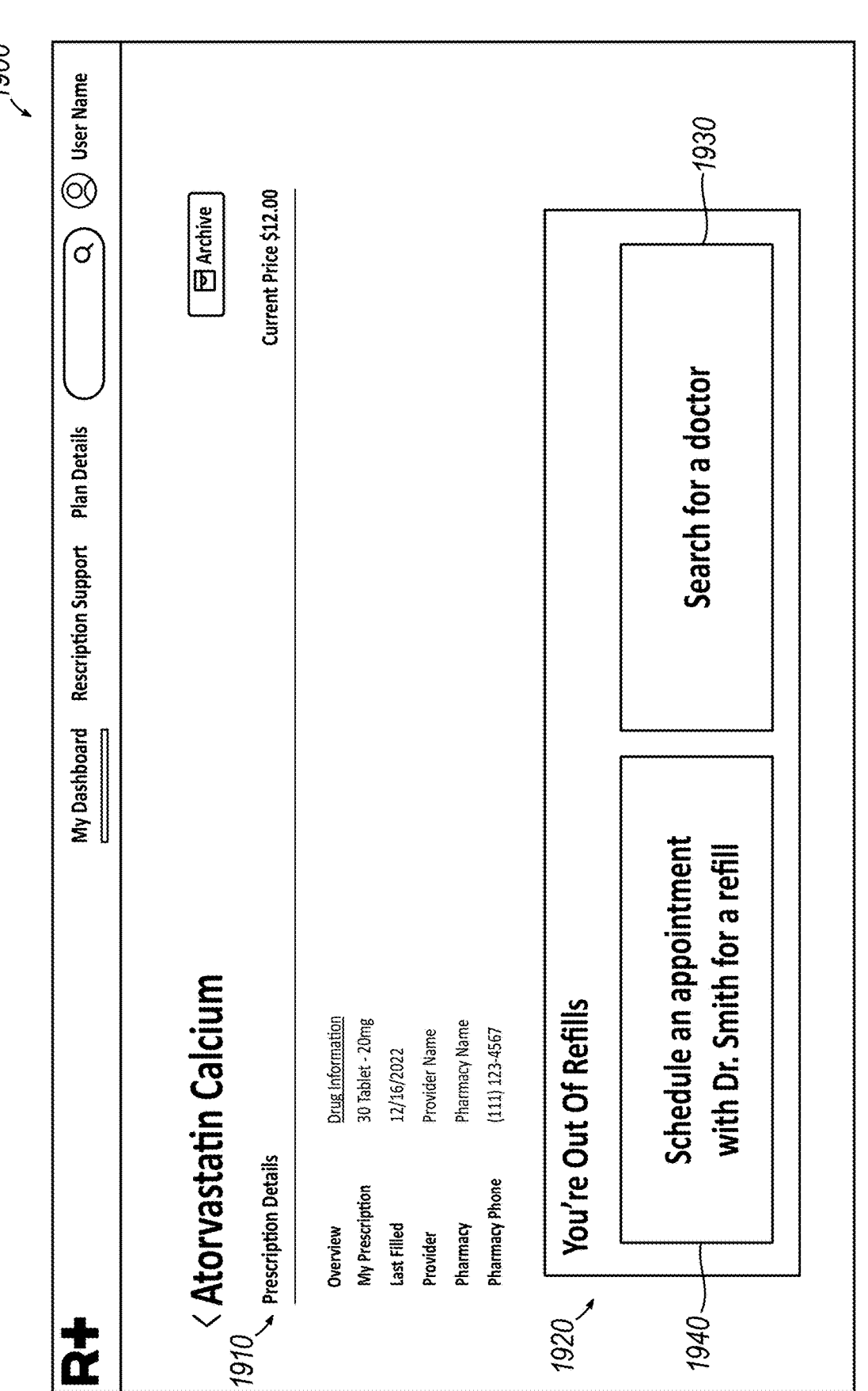
FIG. 10 shows an example embodiment of the user interface of the present disclosure.
Figure 11:
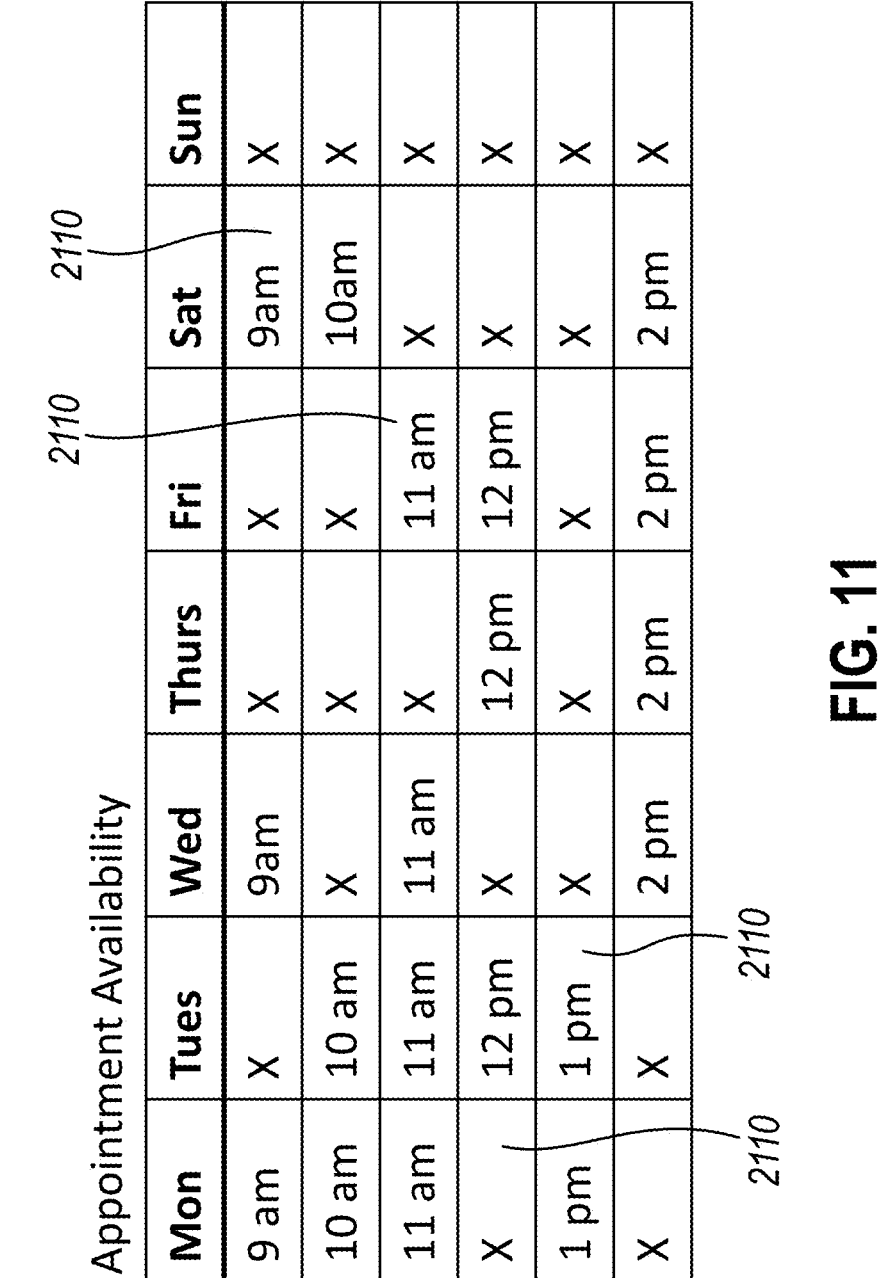
FIG. 11 shows an example embodiment of the user interface of the present disclosure.

In certain embodiments a client may run out of refills of a given prescription. For example, subscription information page 900 of FIG. 5 may indicate to a user that no more refills of a prescription are available. An alternative view of a subscription information page 1900 is shown in FIG. 10. Drug information 1910 can be shown along with a refill notification 1920. The adjudication system 70 of FIG. 1, may provide this indication to the user. The user/client can be presented with a schedule option 1940 to schedule a doctors appointment, and/or a search option 1930 to search for a doctor. Search option 1930 can lead to a search screen such as search screen 1100 adjusted to search for doctors, clinics, Registered Nurses (RNs) or other medical providers that may provide prescription services. Adjudication system 70 may further reach out to doctors' offices near the client, or previous doctors that have prescribed medication for the client. This can include adjudication system 70 searching customer account information 45 or servers 55, contacting medical provider(s) 65 such as doctors' offices or hospitals, health insurance server(s) 60 or contacting other service providers 75 for other information. This process can also involve detecting whether a prescribed/refillable medication is 340b eligible. If so, then adjudication system 70 may prioritize contacting hospital systems via medical providers 65 in order to seek out hospital-based doctor(s) and/or hospital-based pharmacy(ies). Adjudication system 70 may also contact an employer 35 or health insurance provider 60 to determine if there are preferred providers, pharmacies, etc. An employer 35 or health insurance provider 60 may have preferred providers or pharmacies to save money. After receiving a selection by a user/client at subscription information page 1900 (and/or a search screen of doctors), the adjudication system can present the user/client with an appointment scheduling screen. One embodiment of an appointment scheduling screen 2100 is shown in FIG. 11. Here the user can select an available appointment from various appointment options 2110. The appointment data can be received or pulled from e.g., servers comprising medical providers 65.

Figure 12:
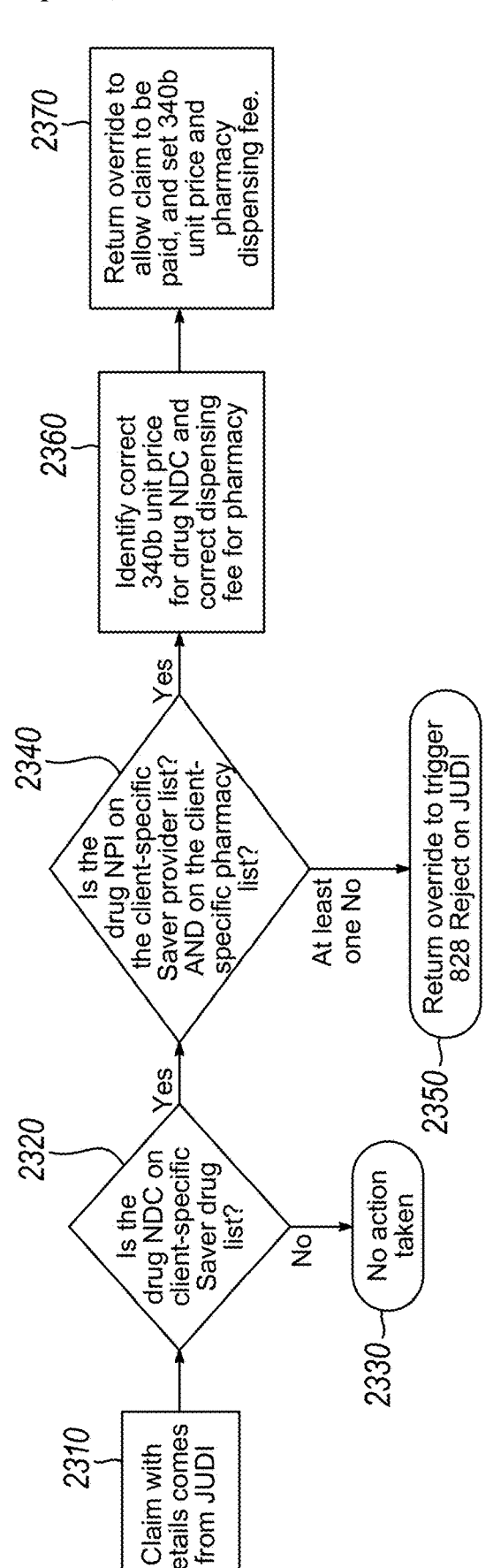
FIG. 12 shows a flow chart of a possible method embodiment under the present disclosure.

A further embodiment under the present disclosure comprises a claim adjudication process 2300 of FIG. 12 performed by e.g., an adjudication system 70 of FIG. 1. At step 2310, a claim with details (e.g., drug, patient, amounts, etc.) is received by the adjudication system from e.g., a pharmacy, a pharmacy benefits manager, etc. At 2320 the system checks if the drug NDC is on a client-specific saver drug list. If not, then no action is taken at 2330. If yes, then at 2340 the system checks if the doctor NPI is on the client-specific saver provider list, and if the pharmacy ID is on a client-specific pharmacy list. If there is at least one 'No,' then at 2350 the process returns override to trigger an 828 rejection on the sending system, e.g., the sending PBM. If both answers are yes at step 2340, then at 2360 the system identifies the correct 340b unit price for the drug NDC and correct dispensing fee for the identified pharmacy. Then at 2370, the system returns override to allow the claim to be paid and sets the 340b unit price and pharmacy dispensing fee.

Figure 13:
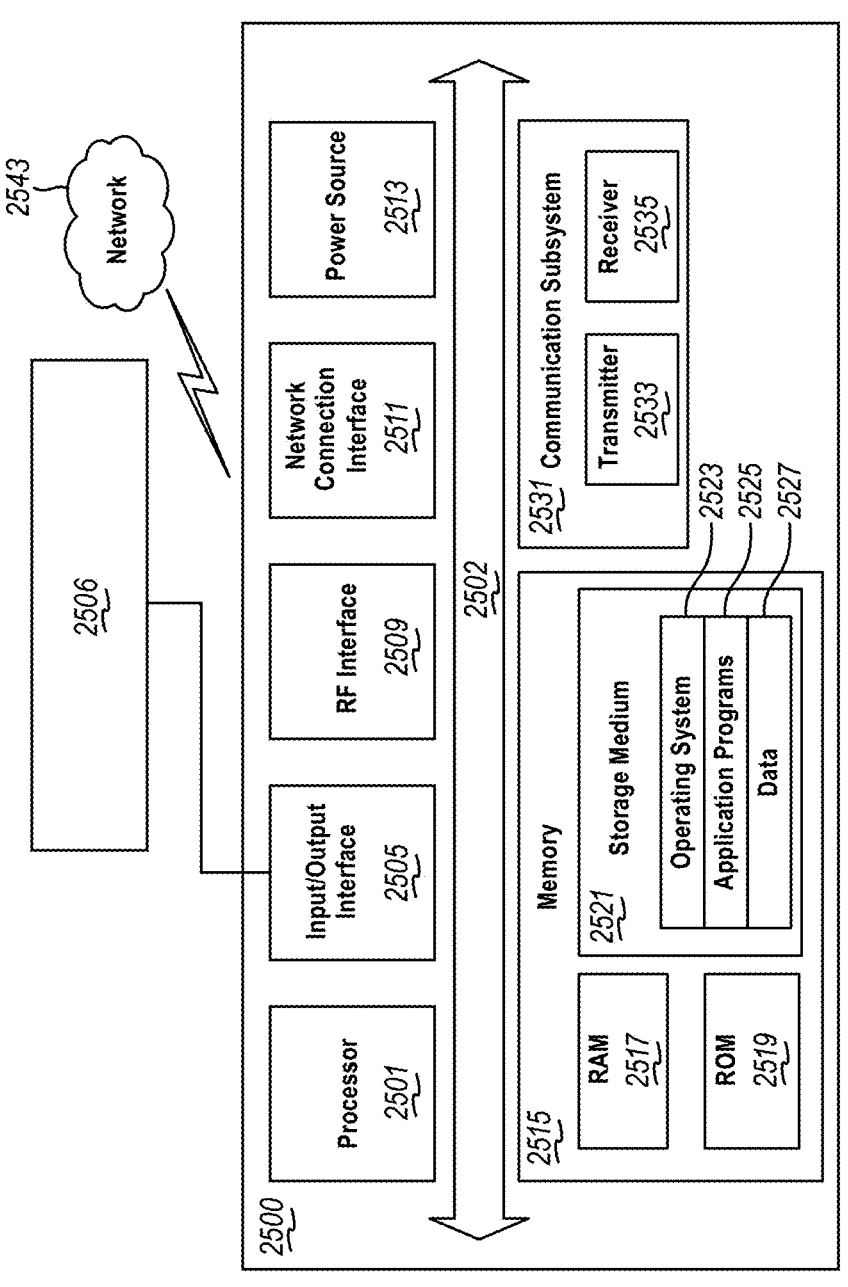
FIG. 13 shows an example embodiment of an adjudication system under the present disclosure.

FIG. 13 illustrates an embodiment of a computing device 2500, capable of performing methods and functionalities described with respect to prescription drug adjudication, fulfillment and inventory system 10 and/or adjudication system 70, or components thereof e.g., computers, databases, servers, mobile devices, laptops, customer account information 45 and other servers 55, configured to implement or perform aspects of the present disclosure. FIG. 13 shows a schematic block diagram of a computing device 2500 (or components thereof) according to certain embodiments of the present disclosure. Computing device 2500 can be used to analyze and/or optimize:

Perform claim adjudication tasks;

Provide intercommunication between e.g., adjudication system 70, customer 5, enterprise 35, health insurance servers 60, medical providers 65, service providers 75, government servers 40, and pharmacy servers 30 of FIG. 1;

Retrieve patient information;

Retrieve doctor or other provider information;

Retrieve appointment information;

Perform artificial intelligence (AI) and/or machine learning (ML) tasks and analyses of data; and/or Other related tasks and data analytics.

Computing device 2500 includes processor 2501 that is operatively coupled via a bus 2502 to an input/output interface 2505, a power source 2513, a memory 2515, a RF interface 2509, network communication interface 2511, and/ or any other component, or any combination thereof. Certain computing devices 2500 may utilize all or a subset of the components shown in FIG. 13. The level of integration between the components may vary from one embodiment to another. Further, certain computing devices 2500 (e.g., adjudication system 70 or components thereof) may contain multiple instances of a component, such as multiple processors, memories, transceivers, transmitters, receivers, etc.

The processor 2501 is configured to process instructions and data and may be configured to implement any sequential state machine operative to execute instructions stored as machine-readable computer programs in memory 2515. Processor 2501 may be implemented as one or more hardware-implemented state machines (e.g., in discrete logic, field-programmable gate arrays (FPGAs), application specific integrated circuits (ASICs), etc.); programmable logic together with appropriate firmware; one or more stored computer programs, general-purpose processors, such as a microprocessor or digital signal processor (DSP), together with appropriate software; or any combination of the above. For example, the processor 2501 may include multiple central processing units (CPUs).

In the example, input/output interface 2505 may be configured to provide an interface or interfaces to an input device, output device, or one or more input and/or output devices, such as screen 2506. Examples of an output device include a speaker, a sound card, a video card, a display, a monitor, a printer, an actuator, an emitter, a smartcard, another output device, or any combination thereof. An input device may allow a user to capture information into system 2500. Examples of an input device include a touch-sensitive or presence-sensitive display, a camera (e.g., a digital camera, a digital video camera, a web camera, etc.), a microphone, a sensor, a mouse, a trackball, a directional pad, a trackpad, a scroll wheel, a smartcard, and the like. The presence-sensitive display may include a capacitive or resistive touch sensor to sense input from a user. A sensor may be, for instance, an accelerometer, a gyroscope, a tilt sensor, a force sensor, a magnetometer, an optical sensor, a proximity sensor, a biometric sensor, etc., or any combination thereof. An output device may use the same type of interface port as an input device. For example, a Universal Serial Bus (USB) port may be used to provide an input device and an output device.

In some embodiments, the power source 2513 is structured as a battery or battery pack. Other types of power sources, such as an external power source (e.g., an electricity outlet), photovoltaic device, or power cell, may be used. The power source 2513 may further include power circuitry for delivering power from the power source 2513 itself, and/or an external power source, to the various parts of adjudication system 2500 via input circuitry or an interface such as an electrical power cable.

Memory 2515 may be configured to include memory such as random access memory (RAM) 2517, read-only memory (ROM) 2519, programmable read-only memory (PROM), erasable programmable read-only memory (EPROM), electrically erasable programmable read-only memory (EEPROM), magnetic disks, optical disks, hard disks, removable cartridges, flash drives, other storage medium 2521, and so forth. In one example, the memory 2515 includes one or more application programs 2525, an operating system 2523, web browser application, a widget, gadget engine, or other application, and corresponding data 2527. Memory 2515 may store, for use by the computing device 2500, any of a variety of various operating systems or combinations of operating systems. An article of manufacture, such as one including a simulation system or communication system may be tangibly embodied as or in memory 2515, which may be or comprise a device-readable storage medium.

Processor 2501 may be configured to communicate with an access network or other network using the RF interface 2509 or network connection interface 2511. The RF interface 2509 or network connection interface 2511 may comprise one or more communication subsystems and may include or be communicatively coupled to an antenna. In the illustrated embodiment, communication functions of the RF interface 2509 or network connection interface 2511 may include cellular communication, Wi-Fi communication, LPWAN communication, data communication, voice communication, multimedia communication, short-range communications such as Bluetooth, near-field communication, location-based communication such as the use of the global positioning system (GPS) to determine a location, another like communication function, or any combination thereof.

Computing device 2500 can perform methods such as methods 1300, 1500, 1700 and 2300. It may perform other AI/ML-based methods as described further below, for e.g., analyzing patient and drug information to extract relationships. For example, for patients on a given drug, there may be a likelihood that they are on another specific drug. Benefits or disadvantages, such as how long the drug use is predicted to last based on specific drug interactions, may be determined by AI/ML analyses. It is possible that patient demographics like gender, race, age, social determinants of health, or other factors may play a role in how effective certain drugs or drug combinations may be. Optimizing drug combinations, or drug effectiveness for certain patients, may lead to savings over time. In certain embodiments, the computing device 2500 can comprise an AI/ML engine for training or implementing a AI/ML model. The architecture of an AI/ML model (e.g., structure, number of layers, nodes per layer, activation function etc.) may need to be tailored for each particular use case. For example, properties to vary can include e.g.: patient age; patient gender; patient race; drug name; drug amount; drug timing/duration; and/or other data which can impact optimization of prescription drug use or cost. These may all need to be considered when designing the ML model's architecture.

Figure 14:
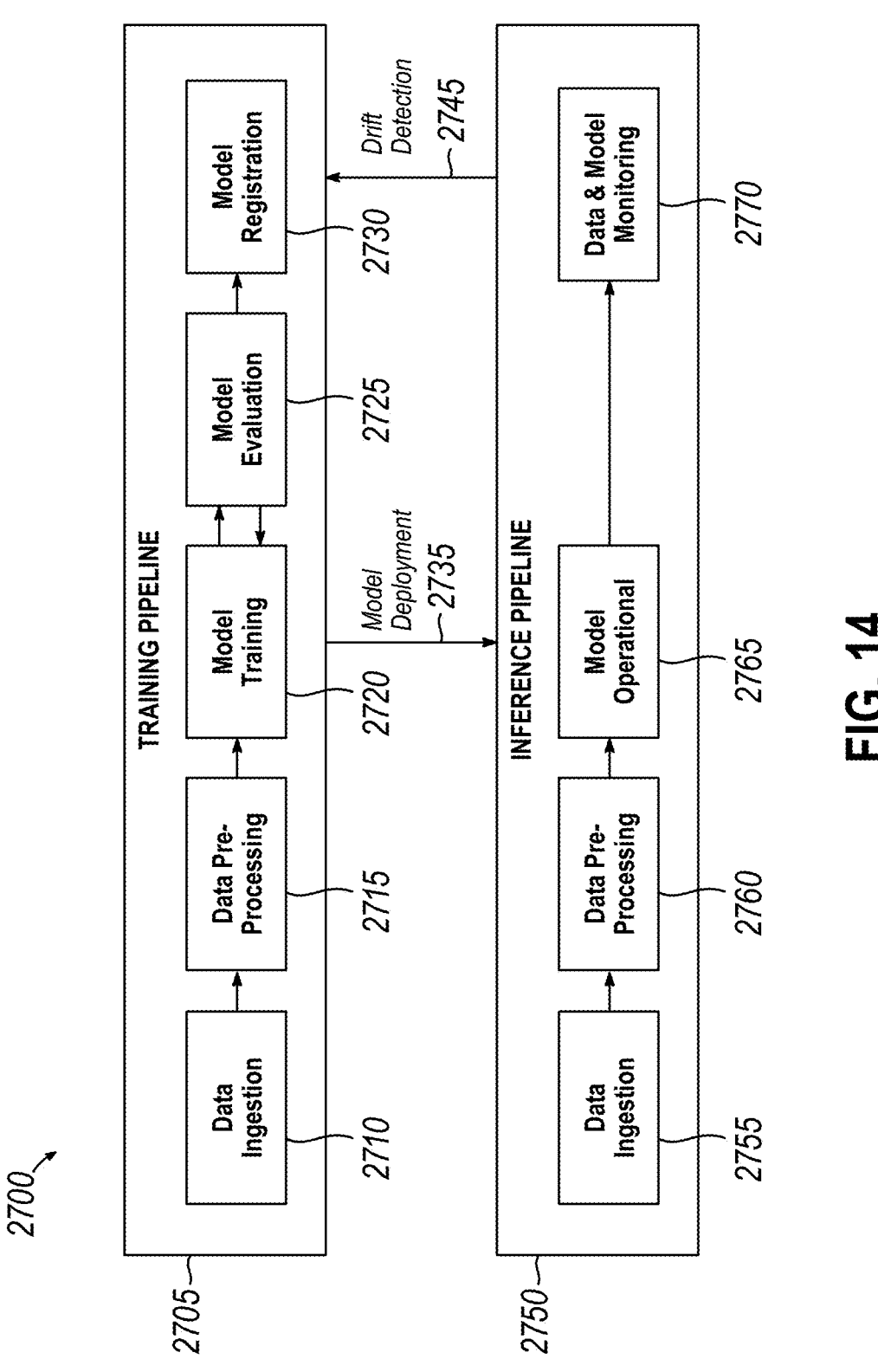
FIG. 14 shows a flow chart of a possible method embodiment under the present disclosure.

Building an AI/ML model includes several development steps where the actual training of the ML model is just one step in a training pipeline. An important part in AI/ML development is the AI/ML model lifecycle management. One embodiment of a model lifecycle management procedure 2700 is illustrated in FIG. 14. The model lifecycle management comprises two pipelines: a training pipeline 2705 and an inference pipeline 2750.

At 2710 in the training pipeline 2705, data ingestion 2710 occurs, which includes gathering raw (training) data from a data storage. After data ingestion 2710, there may also be a step that controls the validity of the gathered data. At 2715 data pre-processing occurs, which can include feature engineering applied to the gathered data. This may involve, e.g., data normalization or data formatting or transformation required for the input data to the AI/ML model. After the ML model's architecture is fixed, it should be trained on one or more datasets. At 2720 model training is performed in which the AI/ML model is trained with the raw training data. To achieve good performance during live operation in a system (the so-called inference phase), the training datasets should be representative of actual data the ML model will encounter during live operation. The training process often involves numerically tuning the ML model's trainable parameters (e.g., the weights and biases of the underlying neural network (NN)) to minimize a loss function on the training datasets. The loss function may be, for example, based on a maximum/minimum spend on drugs, a maximum/minimum duration of use, or other output. The purpose of the loss function is to meaningfully quantify the reconstruction error for the particular use case at hand. At 2725 model evaluation can be performed where the performance is benchmarked to some baseline. Model training 2720 and evaluation 2725 can be iterated until an acceptable level of performance is achieved. At 2730 model registration occurs, in which the AI/ML model is registered with any corresponding data on how the AI/ML model was developed, and e.g., AI/ML model evaluation data. At 2735 model deployment occurs, wherein the trained/re-trained AI/ML model is implemented in the inference pipeline 2750.

Data ingestion 2755 in the inference pipeline 2750 refers to gathering raw (inference) data from a data source. Data pre-processing 2760 can be essentially identical/similar to the data pre-processing 2715 of the training pipeline 2705. At 2765, the operational model received from the training pipeline 2705 is used to process new data received during operation of e.g., adjudication system 2500 of FIG. 13 or 70 of FIG. 1. At 2770 data and model monitoring is performed. Here the inference data is analyzed to determine whether the inference data are from a distribution that aligns with the training data, as well as monitoring model outputs for detecting any performance, or operational, variance or drifts. The variance or drift is used at 2745 (drift detection) to update the AI/ML model registration.

The training process is typically based on some variant of a gradient descent algorithm, which, at its core, can comprise three components: a feedforward step, a back propagation step, and a parameter optimization step. These steps can be described using a dense ML model (i.e., a dense NN with a bottleneck layer) as an example.

Feedforward: A batch of training data, such as a mini-batch, (e.g., several downlink-channel estimates) is pushed through the ML model, from the input to the output. The loss function is used to compute the reconstruction loss for all training samples in the batch. The reconstruction loss may be an average reconstruction loss for all training samples in the batch.

The feedforward calculations of a dense ML model with N layers (n=1, 2, . . . , N) may be written as follows: The output vector $a^{[n]}$ of layer n is computed from the output of the previous layer $a^{[n-1]}$ using the equations:

$$z^{[n]} = W^{[n]} \cdot a^{[n-1]} + b^{[n]}, \; a^{[n]} = g\left(z^{[n]}\right) \qquad (1)$$

In the above equation, $W^{[n]}$ and $b^{[n]}$ are the trainable weights and biases of layer n, respectively, and g is an activation function applied elementwise (for example, a rectified linear unit).

Back propagation (BP): The gradients (partial derivatives of the loss function, L, with respect to each trainable parameter in the ML model) are computed. The back propagation algorithm sequentially works backwards from the ML model output, layer-by-layer, back through the ML model to the input. The back propagation algorithm is built around the chain rule for differentiation: When computing the gradients for layer n in the ML model, it uses the gradients for layer n+1.

For a dense ML model with N layers the back propagation calculations for layer n may be expressed with the following well-known equations:

$$\frac{\partial L}{\partial a^{[n]}} = \left[W^{[n+1]}\right]^T \cdot \frac{\partial L}{\partial z^{[n+1]}} \qquad (2)$$

$$\frac{\partial L}{\partial z^{[n]}} = \frac{\partial L}{\partial a^{[n]}} * g^{[n]\prime}\left(z^{[n]}\right) \qquad (3)$$

$$\frac{\partial L}{\partial W^{[n]}} = \frac{\partial L}{\partial z^{[n]}} \cdot \left[a^{[n-1]}\right]^T \qquad (4)$$

$$\frac{\partial L}{\partial b^{[n]}} = \frac{\partial L}{\partial z^{[n]}} \qquad (5)$$

where * here denotes the Hadamard multiplication of two vectors.

Parameter optimization: The gradients computed in the back propagation step are used to update the ML model's trainable parameters. An approach is to use the gradient descent method with a learning rate hyperparameter (a) that scales the gradients of the weights and biases, as illustrated by the following update equations:

$$W^{[n]} = W^{[n]} - \alpha \cdot \frac{\partial L}{\partial W^{[n]}} \qquad (6)$$

$$b^{[n]} = b^{[n]} - \alpha \cdot \frac{\partial L}{\partial b^{[n]}} \qquad (7)$$

It is preferred to make small adjustments to each parameter with the aim of reducing the average loss over the (mini) batch. It is common to use special optimizers to update the ML model's trainable parameters using gradient information. The following optimizers are widely used to reduce training time and improving overall performance: adaptive sub-gradient methods (AdaGrad), RMSProp, and adaptive moment estimation (ADAM).

The above process (feedforward, back propagation, parameter optimization) is repeated many times until an acceptable level of performance is achieved on the training dataset. An acceptable level of performance may refer to the ML model achieving a pre-defined average reconstruction error over the training dataset (e.g., normalized MSE of the reconstruction error over the training dataset is less than, say, 0.1). Alternatively, it may refer to the ML model achieving a pre-defined value chosen by a user.

In some implementations, a function F(•) may be generated by a ML process, such as, for example, supervised learning, reinforcement learning, and/or unsupervised learning. It should further be understood that supervised learning may be done in various ways, such as, for example, using random forests, support vector machines, neural networks, and the like. By way of non-limiting example, any of the following types of neural networks that may be utilized, including, deep neural networks (DNNs), convolutional neural networks (CNNs), and recurrent neural networks (RNNs), or any other known or future neural network that satisfies the needs of the system. In an implementation using supervised learning the neural networks may be easily integrated into the hardware described in adjudication system 2500 of FIG. 13 (e.g., in the form of simple vector-matrix multiplications).

Figure 15:
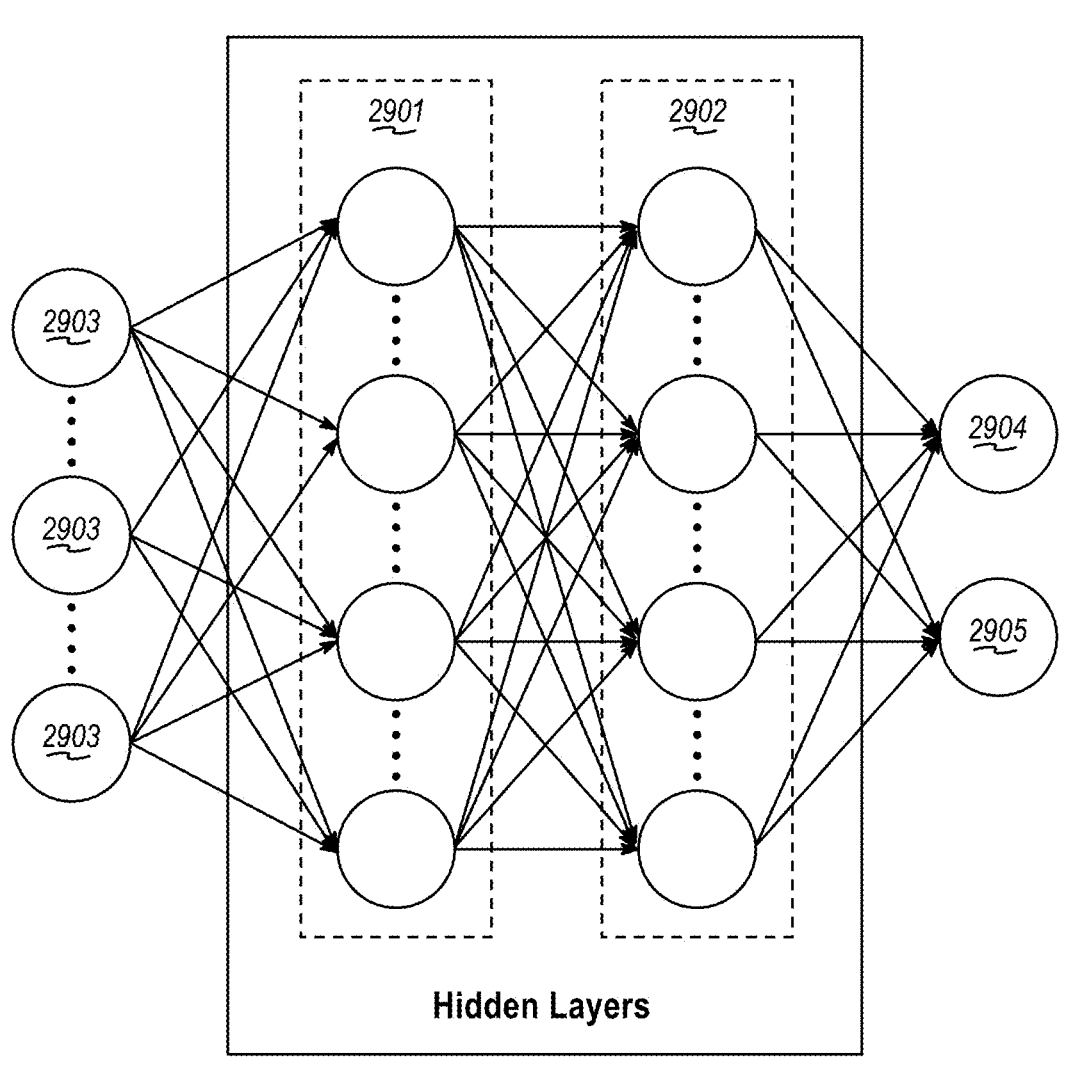
FIG. 15 shows an embodiment of a neural network under the present disclosure.

Referring now to FIG. 15, an example NN 2900 (e.g., DNN) is shown. In some implementations, and as shown, the neural network 2900 may include two hidden layers represented by dashed boxes 2901 and 2902. In one implementation, the inputs 2903 may be fed into the NN 2900. Next, the inputs 2403 may go through a set of hidden layers (e.g., 2901 and/or 2902). Once the inputs 2903 pass though the hidden layers 2901 and/or 2902, they may be output (e.g., as an output layer) as e.g., the likelihoods of a bad drug interaction 2904; likelihood of recovery from disease 2905; or another output valuable for e.g., medical, drug, or patient analysis. Possible inputs can include e.g.: patient age; patient gender; patient race; drug name; drug amount; drug timing/duration; and/or other data which can impact optimization of prescription drug use or cost; or a myriad of other data.

As should be understood by one of ordinary skill in the art, in order for the NN 2900 to output proper a proper analysis, it should be trained properly (e.g., with a collection of samples) to accurately extract the likelihood values. If not trained properly, overfitting (e.g., when the NN memorizes the structure of the preambles but is unable to generalize to unseen preamble characteristics) or underfitting (e.g., when the NN is unable to learn a proper function even on the data that it was trained on) may happen. Thus, implementations may exist that prevent overfitting or underfitting, involving a set of well-engineered features that must be extracted from the preamble characteristics.

A possible AI/ML method embodiment under the present disclosure is shown in FIG. 16. Method 3100 comprises a computer implemented method for training a machine learning model for optimizing prescription drug claim adjudication. Method 3100 could be performed e.g., by adjudication system 70 of FIG. 1 or 2500 of FIG. 13. Step 3110 is obtaining a dataset of identified prescription drug claim adjudication outcomes. Step 3120 is training the machine learning model using the dataset of identified prescription drug claim adjudication outcomes thereby obtaining a trained machine learning model. Step 3130 is storing the trained machine learning model. Method 3100 can comprise multiple variations and additional and/or alternative steps. For example, the previous steps dealt with the ML training pipeline. Further optional steps could deal with inference steps for training a machine learning model for optimizing health outcomes or minimizing prescription costs. The training could comprise optional step 3140, training the machine learning model using a dataset of one or more prescription drug claim adjudication outcomes, thereby obtaining a further trained machine learning model. Optional step 3150 can comprise storing the further trained machine learning model. In some variations the ML model can be a NN, but other types are possible.

Figure 17:
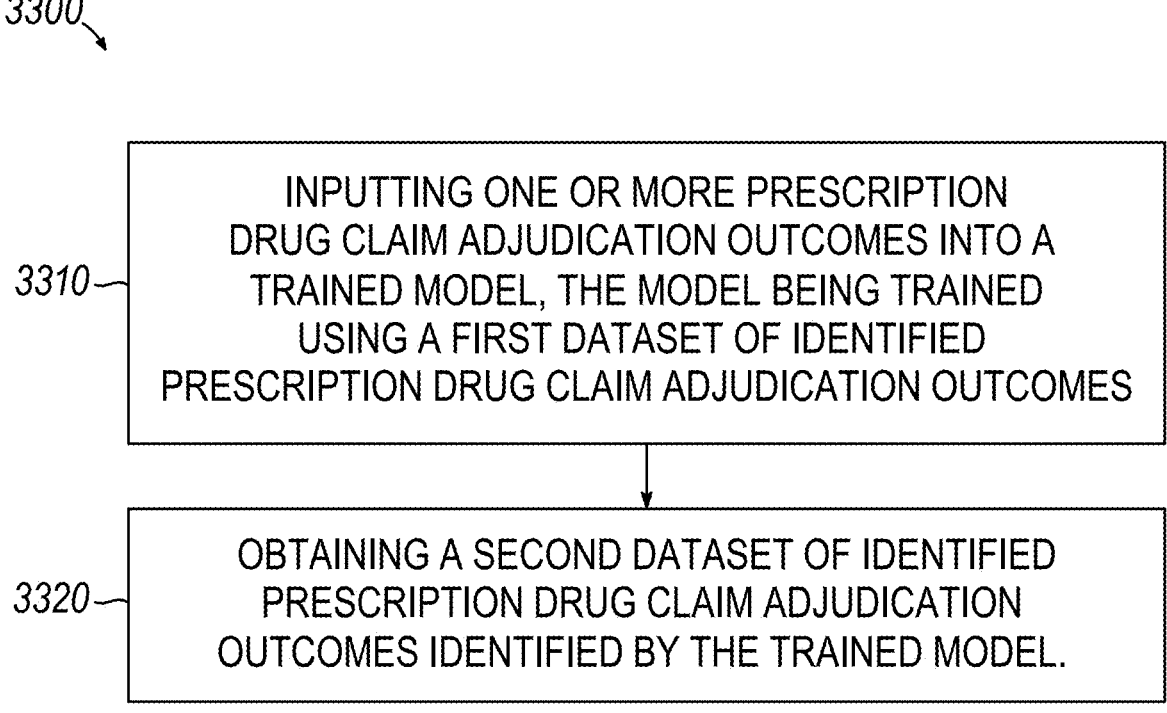
FIG. 17 illustrates a flow-chart of a method embodiment under the present disclosure.

Another possible method embodiment under the present disclosure is shown in FIG. 17. Method 3300 comprises a computer implemented method for obtaining identified prescription drug claim adjudication outcomes (basically a method for inference steps). Step 3310 is inputting one or more prescription drug claim adjudication outcomes into a trained model, the model being trained using a first dataset of identified prescription drug claim adjudication outcomes. Step 3320 is obtaining a second dataset of identified prescription drug claim adjudication outcomes identified by the trained model. Method 3300 can comprise multiple alternative embodiments with additional or alternative steps or other variations.

Another possible method embodiment under the present disclosure is shown in FIG. 18. While certain embodiments have focused on 340b scenarios, other embodiments may include determining drug, patient, health/insurance provider, or employer eligibility for a variety of programs, and how such programs may impact price or availability. Method 3500 is a computer implemented method for adjudicating prescription drug claims. Step 3510 is receiving one or more prescriptions from the one or more medical providers. Step 3520 is confirming if the one or more prescriptions, pharmacies, or patients are eligible according to one or more identified programs. Step 3530 is performing a price search among the one or more pharmacies for the one or more prescriptions, taking into account one or more benefits of the one or more identified programs. Step 3540 is presenting price search results to the one or more patients based on the one or more identified programs. Method 3500 can comprise multiple alternative embodiments with additional or alternative steps or other variations.

Although the computing devices described herein (e.g., computers, databases, servers, mobile devices, etc.) may include the illustrated combination of hardware components, other embodiments may comprise computing devices with different combinations of components. It is to be understood that these computing devices may comprise any suitable combination of hardware and/or software needed to perform the tasks, features, functions and methods disclosed herein. Determining, calculating, obtaining or similar operations described herein may be performed by processing circuitry, which may process information by, for example, converting the obtained information into other information, comparing the obtained information or converted information to information stored therein or elsewhere, and/or performing one or more operations based on the obtained information or converted information, and as a result of said processing making a determination. Moreover, while components are depicted as single boxes located within a larger box, or nested within multiple boxes, in practice, computing devices may comprise multiple different physical components that make up a single illustrated component, and functionality may be partitioned between separate components. For example, a communication interface may be configured to include any of the components described herein, and/or the functionality of the components may be partitioned between the processing circuitry and the communication interface. In another example, non-computationally intensive functions of any of such components may be implemented in software or firmware and computationally intensive functions may be implemented in hardware.

In certain embodiments, some or all of the functionality described herein may be provided by processing circuitry executing instructions stored on in memory, which in certain embodiments may be a computer program product in the form of a non-transitory computer-readable storage medium. In alternative embodiments, some or all of the functionality may be provided by the processing circuitry without executing instructions stored on a separate or discrete device-readable storage medium, such as in a hard-wired manner. In any of those particular embodiments, whether executing instructions stored on a non-transitory computer-readable storage medium or not, the processing circuitry can be configured to perform the described functionality. The benefits provided by such functionality are not limited to the processing circuitry alone or to other components of the computing device, but are enjoyed by the computing device as a whole, and/or by end users and a wireless network generally.

It will be appreciated that computer systems are increasingly taking a wide variety of forms. In this description and in the claims, the terms "controller," "computer system," or "computing system" are defined broadly as including any device or system—or combination thereof—that includes at least one physical and tangible processor and a physical and tangible memory capable of having thereon computer-executable instructions that may be executed by a processor. By way of example, not limitation, the term "computer system" or "computing system," as used herein is intended to include personal computers, desktop computers, laptop computers, tablets, hand-held devices (e.g., mobile telephones, PDAs, pagers), microprocessor-based or programmable consumer electronics, minicomputers, mainframe computers, multi-processor systems, network PCs, distributed computing systems, datacenters, message processors, routers, switches, and even devices that conventionally have not been considered a computing system, such as wearables (e.g., glasses).

The computing system also has thereon multiple structures often referred to as an "executable component." For instance, the memory of a computing system can include an executable component. The term "executable component" is the name for a structure that is well understood to one of ordinary skill in the art in the field of computing as being a structure that can be software, hardware, or a combination thereof. For instance, when implemented in software, one of ordinary skill in the art would understand that the structure of an executable component may include software objects, routines, methods, and so forth, that may be executed by one or more processors on the computing system, whether such an executable component exists in the heap of a computing system, or whether the executable component exists on computer-readable storage media. The structure of the executable component exists on a computer-readable medium in such a form that it is operable, when executed by one or more processors of the computing system, to cause the computing system to perform one or more functions, such as the functions and methods described herein. Such a structure may be computer-readable directly by a processor—as is the case if the executable component were binary. Alternatively, the structure may be structured to be interpretable and/or compiled—whether in a single stage or in multiple stages-so as to generate such binary that is directly interpretable by a processor.

The terms "component," "service," "engine," "module," "control," "generator," or the like may also be used in this description. As used in this description and in this case, these terms—whether expressed with or without a modifying clause—are also intended to be synonymous with the term "executable component" and thus also have a structure that is well understood by those of ordinary skill in the art of computing.

In terms of computer implementation, a computer is generally understood to comprise one or more processors or one or more controllers, and the terms computer, processor, and controller may be employed interchangeably. When provided by a computer, processor, or controller, the functions may be provided by a single dedicated computer or processor or controller, by a single shared computer or processor or controller, or by a plurality of individual computers or processors or controllers, some of which may be shared or distributed. Moreover, the term "processor" or "controller" also refers to other hardware capable of performing such functions and/or executing software, such as the example hardware recited above.

In general, the various exemplary embodiments may be implemented in hardware or special purpose chips, circuits, software, logic, or any combination thereof. For example, some aspects may be implemented in hardware, while other aspects may be implemented in firmware or software which may be executed by a controller, microprocessor, or other computing device, although the disclosure is not limited thereto. While various aspects of the exemplary embodiments of this disclosure may be illustrated and described as block diagrams, flow charts, or using some other pictorial representation, it is well understood that these blocks, apparatus, systems, techniques, or methods described herein may be implemented in, as non-limiting examples, hardware, software, firmware, special purpose circuits or logic, general purpose hardware or controller or other computing devices, or some combination thereof.

While not all computing systems require a user interface, in some embodiments a computing system includes a user interface for use in communicating information from/to a user. The user interface may include output mechanisms as well as input mechanisms. The principles described herein are not limited to the precise output mechanisms or input mechanisms as such will depend on the nature of the device. However, output mechanisms might include, for instance, speakers, displays, tactile output, projections, holograms, and so forth. Examples of input mechanisms might include, for instance, microphones, touchscreens, projections, holograms, cameras, keyboards, stylus, mouse, or other pointer input, sensors of any type, and so forth.

Abbreviations and Defined Terms

To assist in understanding the scope and content of this written description and the appended claims, a select few terms are defined directly below. Unless defined otherwise, all technical and scientific terms used herein have the same meaning as commonly understood by one of ordinary skill in the art to which the present disclosure pertains.

The terms "approximately," "about," and "substantially," as used herein, represent an amount or condition close to the specific stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a specifically stated amount or condition.

Various aspects of the present disclosure, including devices, systems, and methods may be illustrated with reference to one or more embodiments or implementations, which are exemplary in nature. As used herein, the term "exemplary" means "serving as an example, instance, or illustration," and should not necessarily be construed as preferred or advantageous over other embodiments disclosed herein. In addition, reference to an "implementation" of the present disclosure or embodiments includes a specific reference to one or more embodiments thereof, and vice versa, and is intended to provide illustrative examples without limiting the scope of the present disclosure, which is indicated by the appended claims rather than by the present description.

As used in the specification, a word appearing in the singular encompasses its plural counterpart, and a word appearing in the plural encompasses its singular counterpart, unless implicitly or explicitly understood or stated otherwise. Thus, it will be noted that, as used in this specification and the appended claims, the singular forms "a," "an" and "the" include plural referents unless the context clearly dictates otherwise. For example, reference to a singular referent (e.g., "a widget") includes one, two, or more referents unless implicitly or explicitly understood or stated otherwise. Similarly, reference to a plurality of referents should be interpreted as comprising a single referent and/or a plurality of referents unless the content and/or context clearly dictate otherwise. For example, reference to referents in the plural form (e.g., "widgets") does not necessarily require a plurality of such referents. Instead, it will be appreciated that independent of the inferred number of referents, one or more referents are contemplated herein unless stated otherwise.

References in the specification to "one embodiment," "an embodiment," "an example embodiment," and the like indicate that the embodiment described may include a particular feature, structure, or characteristic, but it is not necessary that every embodiment includes the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

It shall be understood that although the terms "first" and "second" etc. may be used herein to describe various elements, these elements should not be limited by these terms. These terms are only used to distinguish one element from another. For example, a first element could be termed a second element, and similarly, a second element could be termed a first element, without departing from the scope of example embodiments. As used herein, the term "and/or" includes any and all combinations of one or more of the associated listed terms.

It will be further understood that the terms "comprises", "comprising", "has", "having", "includes" and/or "including", when used herein, specify the presence of stated features, elements, and/or components etc., but do not preclude the presence or addition of one or more other features, elements, components and/or combinations thereof.

CONCLUSION

The present disclosure includes any novel feature or combination of features disclosed herein either explicitly or any generalization thereof. Various modifications and adaptations to the foregoing exemplary embodiments of this disclosure may become apparent to those skilled in the relevant arts in view of the foregoing description, when read in conjunction with the accompanying drawings. However, any and all modifications will still fall within the scope of the non-limiting and exemplary embodiments of this disclosure.

It is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

In addition, unless otherwise indicated, numbers expressing quantities, constituents, distances, or other measurements used in the specification and claims are to be understood as being modified by the term "about," as that term is defined herein. Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Any headings and subheadings used herein are for organizational purposes only and are not meant to be used to limit the scope of the description or the claims. The terms and expressions which have been employed herein are used as terms of description and not of limitation, and there is no intention in the use of such terms and expressions of excluding any equivalents of the features shown and described or portions thereof, but it is recognized that various modifications are possible within the scope of the present disclosure. Thus, it should be understood that although the present disclosure has been specifically disclosed in part by certain embodiments, and optional features, modification and variation of the concepts herein disclosed may be resorted to by those skilled in the art, and such modifications and variations are considered to be within the scope of this present description.

It will also be appreciated that systems, devices, products, kits, methods, and/or processes, according to certain embodiments of the present disclosure may include, incorporate, or otherwise comprise properties or features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

It will be apparent to one of ordinary skill in the art that methods, devices, device elements, materials, procedures, and techniques other than those specifically described herein can be applied to the practice of the described embodiments as broadly disclosed herein without resort to undue experimentation. All art-known functional equivalents of methods, devices, device elements, materials, procedures, and techniques specifically described herein are intended to be encompassed by this present disclosure.

When a group of materials, compositions, components, or compounds is disclosed herein, it is understood that all individual members of those groups and all subgroups thereof are disclosed separately. When a Markush group or other grouping is used herein, all individual members of the group and all combinations and sub-combinations possible of the group are intended to be individually included in the disclosure.

The above-described embodiments are examples only. Alterations, modifications, and variations may be effected to the particular embodiments by those of skill in the art without departing from the scope of the description, which is defined solely by the appended claims.

The invention claimed is:

1. A system for adjudicating prescription drug claims, the system comprising:

one or more adjudication servers configured to store one or more patient records, the one or more adjudication servers comprising one or more communication interfaces configured to communicate with: one or more patients, one or more medical providers, one or more insurance providers, one or more pharmacies, one or more employers related to the one or more patients, and one or more governments servers;

the one or more adjudication servers comprising a memory storing instructions whereby the one or more adjudication servers are configured to:

receive one or more prescriptions from the one or more medical providers;

retrieve eligibility information for each of the one or more prescriptions, in parallel, from the one or more government servers via one or more secure application programming interfaces (APIs) and store the eligibility information in an eligibility database;

confirm, during a refill request, if the one or more prescriptions are 340b eligible according to the eligibility information stored in the eligibility database;

contact the one or more employers related to the one or more patients to determine one or more preferred pharmacies;

receive, during the refill request, a location from a patient;

perform a price search among any of the one or more pharmacies within a predetermined radius of the location for the one or more prescriptions by executing one or more test claims for each of the one or more prescriptions in parallel; and present price search results to the one or more patients with the one or more patient connections, wherein the price search results are based at least in part on the one or more preferred pharmacies.

2. The system of claim 1, wherein the one or more adjudication servers are further configured to:

notify the one or more patients if the one or more prescriptions are out of refills;

perform an appointment search among the one or more medical providers;

present appointment search results to the one or more patients via the one or more patient connections;

receive an appointment selection from the one or more patients; and schedule the appointment selection with a respective of the one or more medical providers.

3. The system of claim 1, wherein the one or more adjudication servers are further configured to train a machine learning model for optimizing health-related outcomes, wherein the training comprises;

training the machine learning model using a dataset of identified health-related outcomes, thereby obtaining a trained machine learning model; and storing the trained machine learning model.

4. The system of claim 3, wherein the one or more adjudication servers are further configured to obtain a dataset of health-related outcomes identified by the trained machine learning model by inputting one or more data points related to the one or more prescriptions or the one or more patients.

5. The system of claim 3, wherein the dataset of identified health-related outcomes includes prescription costs.

6. The system of claim 1, wherein the one or more adjudication servers are further configured to provide a notification to the one or more patients if a lower price is found than a previously paid price.

7. The system of claim 1, wherein the one or more adjudication servers are further configured to display results of the price search in a map showing the one or more pharmacies and respective price at each of the one or more pharmacies.

8. The system of claim 1, wherein the one or more adjudication servers are further configured to perform a periodic price search among the one or more pharmacies for the one or more prescriptions.

9. The system of claim 1, wherein the one or more adjudication servers are further configured to:

receive the refill request from the patient;

receive a pharmacy selection from any of the one or more pharmacies within the predetermined radius;

initiate the refill request with the selected pharmacy.

10. The system of claim 1, wherein the one or more adjudication servers are further configured to:

send a test prescription drug claim to each of the one or more pharmacies, the one or more pharmacies, and the preference pharmacy;

receive results for each test prescription drug claim;

sort the results according to price; and save a lowest price in the results in the one or more prescription drug claims in the one or more adjudication servers.

11. The system of claim 1, wherein the information retrieved from the one or more government servers was previously retrieved.

12. The system of claim 1, wherein the information retrieved from the one or more government servers is retrieved during the fill request.

* * * * *